(12) United States Patent
Colburn et al.

(10) Patent No.: US 9,542,663 B2
(45) Date of Patent: Jan. 10, 2017

(54) MULTI-TAG IDENTIFICATION DEVICES, VARIABLE-POWER STANDOFF READERS FOR SAME, AND RELATED SYSTEMS

(71) Applicant: CAIWD, LLC, Winooski, VT (US)

(72) Inventors: Michael G. Colburn, Burlington, VT (US); Nitai Friedman, Hampstead (CA)

(73) Assignee: CAIWD, LLC, Burlington, VT (US)

( * ) Notice: Subject to any disclaimer, the term of this patent is extended or adjusted under 35 U.S.C. 154(b) by 1 day.

(21) Appl. No.: 14/804,612

(22) Filed: Jul. 21, 2015

(65) Prior Publication Data
US 2015/0324716 A1    Nov. 12, 2015

Related U.S. Application Data

(63) Continuation of application No. 14/351,447, filed as application No. PCT/US2012/059185 on Oct. 8, 2012, now abandoned.
(Continued)

(51) Int. Cl.
*G06Q 10/00*     (2012.01)
*G06Q 10/06*     (2012.01)
(Continued)

(52) U.S. Cl.
CPC ......... *G06Q 10/0639* (2013.01); *G06F 19/327* (2013.01); *G06Q 30/018* (2013.01);
(Continued)

(58) Field of Classification Search
CPC . G06F 19/322; G06Q 10/0639; G06Q 30/018; G06Q 50/22; A61N 1/08; H04W 4/008
See application file for complete search history.

(56) References Cited

U.S. PATENT DOCUMENTS 5,610,589 A    3/1997 Evans et al.
5,812,059 A    9/1998 Shaw et al.
(Continued)

FOREIGN PATENT DOCUMENTS

WO    2008119158 A1    10/2008
WO    2011058292 A1    5/2011
WO    WO2011058292    *    5/2011

OTHER PUBLICATIONS

PCT International Search Report and Written Opinion dated May 30, 2014 for related PCT/US2012/059185 entitled "Sanitization Protocol Monitoring/Compliance Systems, Apparatuses, Methods, and Software," CAIWD, LLC.
(Continued)

*Primary Examiner* — Luke Gilligan
(74) *Attorney, Agent, or Firm* — Downs Rachlin Martin PLLC

(57) ABSTRACT

Systems, apparatuses, methods, and software for monitoring compliance of sanitizees (e.g., health care workers, food service workers, sanitization/janitorial workers etc.) with sanitization protocols to be followed for encounters with sanitization-protocol targets (e.g., patients, food-preparation areas, health care facilities/appurtenances, restrooms, etc.). In one example, a system includes sanitization verification systems located close to the targets and mobile node devices issued to the sanitizees. Each verification system can be configured to test the efficacy of sanitization procedures performed by the sanitizees prior to encountering a target, to provide authorizations, via the node devices, to the sanitizees to proceed with target encounters, and to open monitoring sessions during which the node devices record information concerning interactions with the targets. The node devices are configured to annunciate sanitization statuses of the sanitizees throughout a work period as the sanitizees
(Continued)

continually interact with verification stations and encounter targets.

7 Claims, 7 Drawing Sheets

Related U.S. Application Data

(60) Provisional application No. 61/627,601, filed on Oct. 14, 2011.

(51) Int. Cl.

| | | |
|---|---|---|
| *G06Q 30/00* | (2012.01) | |
| *H04W 4/00* | (2009.01) | |
| *G06F 19/00* | (2011.01) | |
| *G07C 1/10* | (2006.01) | |
| *G06Q 50/22* | (2012.01) | |
| *G08B 21/24* | (2006.01) | |

(52) U.S. Cl.
CPC ............... *G06Q 50/22* (2013.01); *G07C 1/10* (2013.01); *H04W 4/008* (2013.01); *G08B 21/245* (2013.01)

(56) References Cited

U.S. PATENT DOCUMENTS

| | | | |
|---|---|---|---|
| 5,952,924 A | 9/1999 | Evans et al. | |
| 6,975,231 B2 | 12/2005 | Lane et al. | |
| 7,015,816 B2 | 3/2006 | Wildman et al. | |
| 7,375,640 B1 | 5/2008 | Plost | |
| 7,561,977 B2 * | 7/2009 | Horst ........................ | H02J 3/14 |
| | | | 700/295 |
| 7,616,122 B2 | 11/2009 | Bolling | |
| 7,755,494 B2 | 7/2010 | Melker et al. | |
| 7,893,842 B2 | 2/2011 | Deutsch | |
| 7,898,407 B2 | 3/2011 | Hufton et al. | |
| 8,040,245 B2 | 10/2011 | Koblasz | |
| 8,115,600 B2 * | 2/2012 | Stevenson ................ | A61N 1/08 |
| | | | 235/472.01 |
| 8,237,558 B2 | 8/2012 | Seyed Momen et al. | |
| 8,698,637 B2 | 4/2014 | Raichman | |
| 8,799,008 B2 | 8/2014 | Johnson et al. | |
| 2006/0132316 A1 | 6/2006 | Wildman et al. | |
| 2006/0267731 A1 * | 11/2006 | Chen ..................... | G06Q 10/08 |
| | | | 340/10.1 |
| 2008/0001763 A1 | 1/2008 | Raja et al. | |
| 2008/0131332 A1 | 6/2008 | Nguyen et al. | |
| 2008/0246599 A1 | 10/2008 | Hufton et al. | |
| 2009/0089093 A1 | 4/2009 | Johnson et al. | |
| 2009/0219131 A1 | 9/2009 | Barnett et al. | |
| 2009/0224907 A1 | 9/2009 | Sinha et al. | |
| 2009/0236254 A1 | 9/2009 | Jenkins et al. | |
| 2009/0243833 A1 * | 10/2009 | Huang .................. | G06F 19/323 |
| | | | 340/505 |
| 2009/0299787 A1 | 12/2009 | Barnhill | |
| 2010/0073162 A1 | 3/2010 | Johnson et al. | |
| 2010/0134296 A1 | 6/2010 | Hwang | |
| 2010/0262430 A1 | 10/2010 | Gips et al. | |
| 2010/0315243 A1 | 12/2010 | Tokhtuev et al. | |
| 2010/0321180 A1 | 12/2010 | Dempsey et al. | |
| 2010/0328443 A1 | 12/2010 | Lynam et al. | |
| 2011/0148586 A1 | 6/2011 | Anderson et al. | |
| 2011/0234598 A1 | 9/2011 | Scarola et al. | |
| 2011/0263950 A1 * | 10/2011 | Larson .................. | A61B 5/024 |
| | | | 600/301 |
| 2012/0002510 A1 | 1/2012 | Berman, Jr. | |
| 2012/0055986 A1 | 3/2012 | Sahud | |
| 2012/0112906 A1 | 5/2012 | Borke et al. | |
| 2012/0154582 A1 | 6/2012 | Johnson et al. | |
| 2012/0158419 A1 | 6/2012 | Nuthi | |
| 2013/0262060 A1 | 10/2013 | Higashi | |
| 2014/0303996 A1 | 10/2014 | Johnson | |
| 2014/0320289 A1 | 10/2014 | Raichman | |

OTHER PUBLICATIONS

Office Action dated Sep. 26, 2014, issued in connection with related U.S. Appl. No. 14/351,447, filed Apr. 11, 2014.

Final Office Action dated Feb. 27, 2015, issued in connection with related U.S. Appl. No. 14/351,447, filed Apr. 11, 2014.

Advisory Action dated May 22, 2015, issued in connection with related U.S. Appl. No. 14/351,447, filed Apr. 11, 2014.

Levchenko et al., titled "The Feasibility of an Automated Monitoring System to Improve Nurses' Hand Hygiene," International Journal of Medical Informatics 80 (2011), pp. 296-603.

Dancer, S. J., titled "The role of environmental cleaning in the control of hospital-acquired infection," Journal of Hospital Infection (2009) 73, pp. 378-385.

* cited by examiner

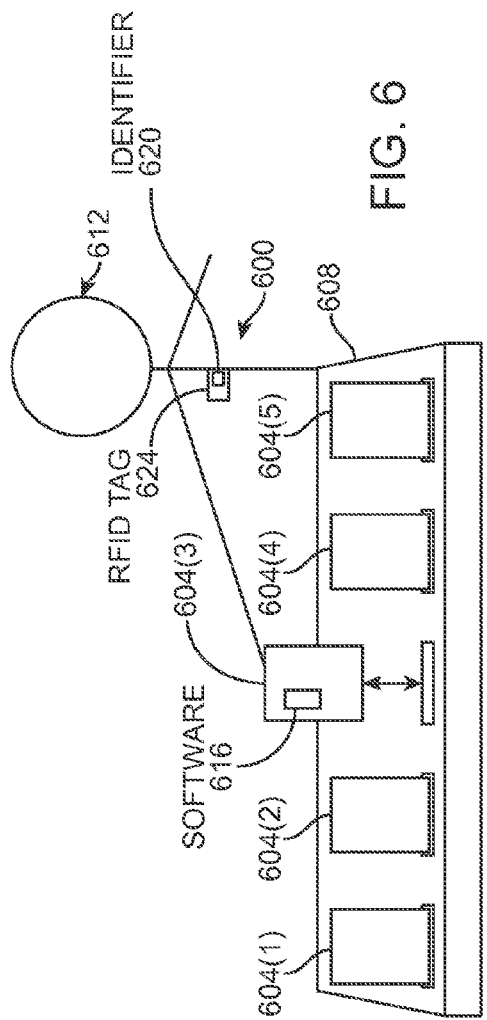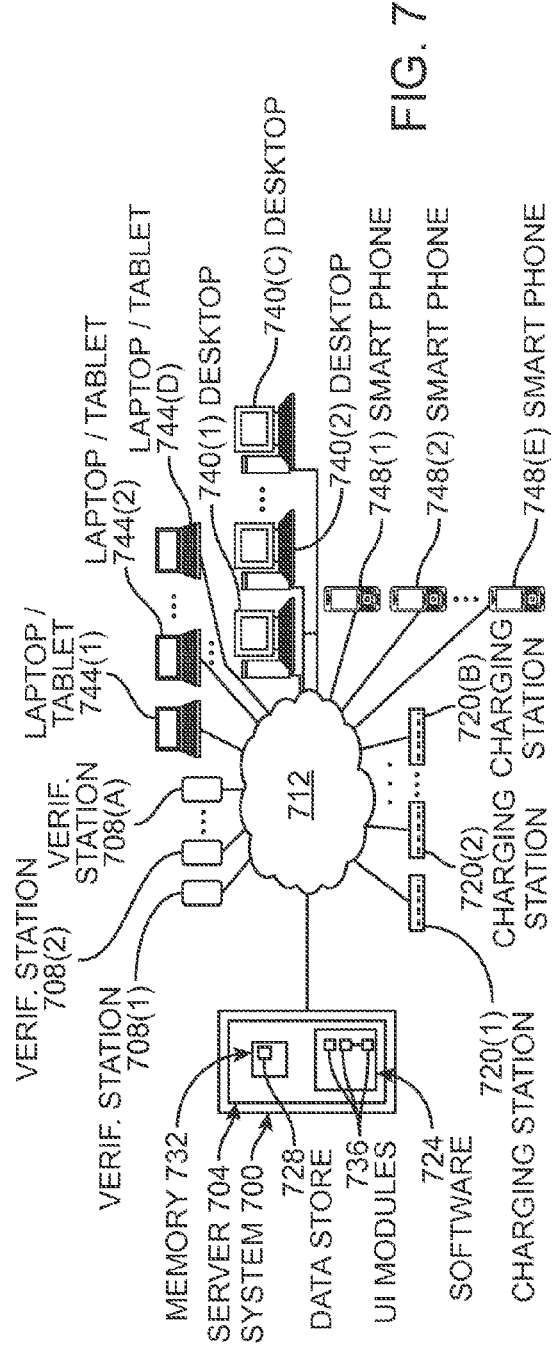

US 9,542,663 B2

MULTI-TAG IDENTIFICATION DEVICES, VARIABLE-POWER STANDOFF READERS FOR SAME, AND RELATED SYSTEMS

RELATED APPLICATION DATA

This application is a continuation application of U.S. Nonprovisional patent application Ser. No. 14/351,447, filed Apr. 11, 2014, and entitled "Sanitization Protocol Adherence Monitoring/Compliance Systems and Methods, and Software and Apparatuses Therefor", which application was a U.S. national phase application of PCT/US12/59185, filed Oct. 8, 2012, and entitled "Sanitization Protocol Adherence Monitoring/Compliance Systems and Methods, and Software and Apparatuses Therefor", and which applications claim the benefit of priority of U.S. Provisional Patent Application Ser. No. 61/627,601, filed on Oct. 14, 2011, and titled "Hand Sanitation Protocol Monitoring System." Each of these applications is incorporated by reference herein in its entirety.

FIELD OF THE INVENTION

The present invention generally relates to standoff identification systems. In particular, the present invention is directed to multi-tag identification devices, variable-power standoff readers for same, and related systems.

BACKGROUND

Proper sanitation of workers in a variety of fields is important for inhibiting the spread of diseases, infections, germs, bacteria, etc. For example, in the health care field, the World Health Organization (WHO) opened its recent "Guidelines to Hand Hygiene in Health Care" (2009, ISBN 978 92 4 159790 6) with the statement "Health care acquired infections (HCAI) are a major problem for patient safety and its surveillance, and prevention must be a first priority for settings and institutions committed to making health care safer." In the U.S. health care system alone there are an estimated nearly two million incidents where health care patients acquire infectious diseases from being in a health care facility. These infections, sometimes referred to a "nosocomial infections," are unrelated to the patients' reasons for being admitted to their respective facilities. These infections are also labeled "HCAI" (or "HAI" when "healthcare" is written as one word, which is sometimes the case). Around 100,000 of the infected patients in the U.S. die from their HCAIs annually (about 273 people per day). This is greater than the number of people that die from automobile accidents, breast cancer, and AIDS combined. Another field where proper worker sanitization is important is the food service industry, where a single unsanitary worker, food-preparation tool, etc., can sicken many people that ingest food tainted as a result of improper sanitization. Still another field where proper sanitization of workers and their tools in the sanitization/janitorial field where the workers are responsible for sanitizing a variety of facilities, such as health care facilities (human and animal), food service facilities, restroom facilities, and virtually any other facility where infectious matter can be picked up by a human or animal by transmission from an unsanitized or improperly sanitized surface, object, etc., within the corresponding facility.

SUMMARY OF THE DISCLOSURE

In one implementation, the present disclosure is directed to an identification device for identifying a target. The device includes a plurality of linked tags containing identification information identifying the target, each tag: designed and configured to be readable by a standoff reading device; and containing linking information that allows the standoff reading device to associate the plurality of linking tags with one another; and a support structure designed and configured to locate the identification device proximate the target, wherein the plurality of linking tags are supported by the support structure.

In another implementation, the present disclosure is directed to a system for identifying a target. The system includes an identification device for identifying the target, the identification device including: a plurality of linked tags containing identification information identifying the target, each tag: designed and configured to be readable by a standoff reading device; and containing linking information that allows the standoff reading device to associate the plurality of linking tags with one another; and a support structure designed and configured to locate the identification device proximate the target, wherein the plurality of linking tags are supported by the support structure.

In yet another implementation, the present disclosure is directed to a standoff reader designed and configured for use with a plurality of linked radio frequency identification (RFID) tags containing 1) identification information identifying a target associated with the identification device and 2) linking information associating the plurality of linked RFID tags with one another. The standoff reader includes an antenna/transponder system designed and configured to energize each of the plurality of linked RFID tags; a power source operatively connected to the antenna/transponder system and designed and configured to energize the antenna/transponder system with differing tag-energizing powers at differing times; a tag reader designed and configured for reading the identification information and linking information from each of the plurality of linked tags when in reading range; and a power controller operatively connected to the power source and the tag reader, the power controller designed and configured to change the power source from one of the differing tag-energizing powers to another of the differing tag-energizing powers as a function of how many of the plurality of the linked tags the tag reader has identified.

In still yet another implementation, the present disclosure is directed to a system for monitoring a sanitizee with respect to a sanitization protocol for a sanitization-protocol target. The system includes a sanitizee node device designed and configured to: be carried by the sanitizee; and receive a monitoring session authorization that provides the sanitizee node device with permission to recognize a valid sanitizee/sanitization-protocol-target encounter; a sanitization verification system designed and configured to provide the sanitizee node device with the monitoring session authorization; a sanitization-protocol-target identification device associated with the sanitization protocol target, the sanitizee node device including a reader designed and configured to read the sanitization-protocol-target identification device at a standoff distance, the sanitization-protocol-target identification device comprising: a plurality of linked radio frequency identification (RFID) tags each containing a linking sequence that the reader uses to determine that the plurality of linked RFID tags are linked with one another, and a support structure designed and configured to locate the sanitization-protocol-target identification device proximate the sanitization protocol target, wherein the plurality of linking tags are supported by the support structure.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 6 is a diagram of a generic node device system that can be used in a sanitization protocol monitoring/compliance system deployment of the present invention, wherein the system includes a docking/charging station;

FIG. 7 is a block diagram of an exemplary sanitization compliance data processing system that can be used in a sanitization protocol monitoring/compliance system deployment of the present invention;

DETAILED DESCRIPTION

Figure 1:
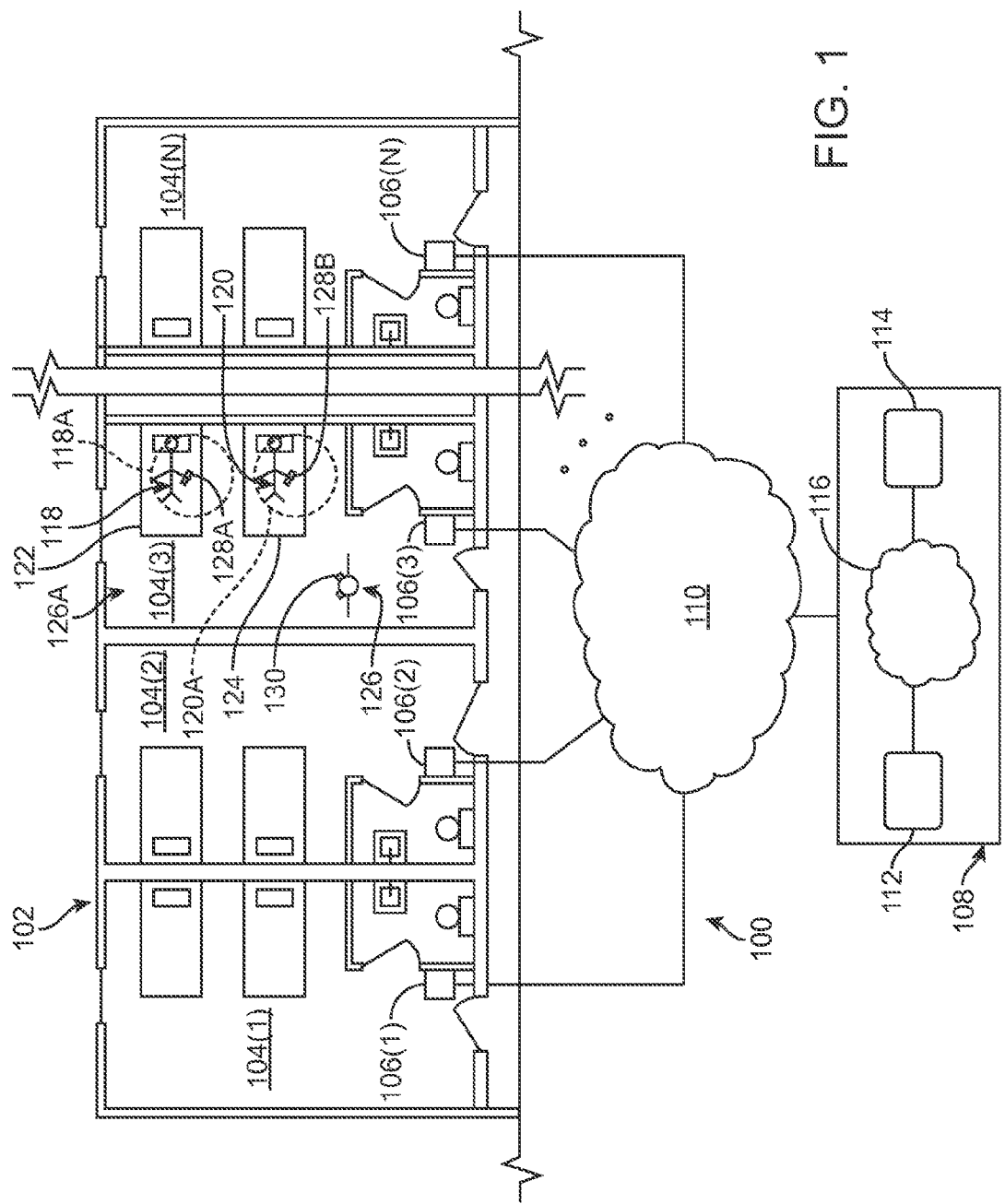
FIG. 1 is a plan view of an exemplary deployment of a sanitization protocol monitoring/compliance system of the present invention.

The present invention encompasses many aspects, features, and embodiments that can be instantiated in any of a variety of ways, such as systems, apparatuses, methods, and software. A number of these aspects, features, and embodiments are illustrated below. However, because of the fair amount of complexity attendant to actual instantiations of the present invention, the aspects, features, and embodiments are presented below in a way that, while providing specific examples, also convey the general and overarching aspects and features that those skilled in the art can use to create other instantiations that fall within the scope of the present invention and the appended claims. It should be understood that neither the examples provided nor the order of presentation of various aspects, features, components, and embodiments, should necessarily infer order of importance or inventive scope.

In one aspect, the present invention is directed to a method of monitoring compliance of one or more monitored persons (e.g., health care workers, food service workers, sanitization/janitorial workers, etc.) with a pre-established sanitization protocol (e.g., a hand-sanitization protocol, a tool-sanitizing protocol, etc.) for one or more sanitization-protocol targets (e.g., a health care patient, a food-preparation area, health care facility/appurtenance, etc.). An important feature for some of the embodiments is the presence of one or more sanitization verification systems (embodied, e.g., in unitary sanitization verification stations) that provide means for at least testing for the performance of a sanitizing event by a monitored person and, in some cases, actually determining the effectiveness of the sanitization event, before authorizing a monitoring session, i.e., a time period where the monitored person is inferred or assumed to be in a sanitized state and, therefore, authorized to have a sanitized encounter with a sanitization-protocol target. Data collected from the testing performed at the one or more sanitization verification systems can be used in a variety of ways, such as in generating reports that track sanitation compliance of the monitored persons, to notify the monitored person and/or others of the effectiveness of the sanitization, to control the monitored person's actions subsequent to the sanitization event, and any logical combination of these, among other things. These and other benefits of performing verification/effectiveness testing on sanitizing events are described below in connection with detailed examples.

It is noted that while the various aspects, features, and embodiments of the present invention can be applied to a variety of fields, such as the health care field, food service field, and sanitization/janitorial field, for convenience the focus of the following examples is on the health care field. To make these examples more readable, the terms "monitored health care worker" ("MW" for short), "hand-sanitization protocol," and "monitored patient" ("MP" for short), and the like, are used in lieu of the more general terms "monitored persons," "pre-established sanitization protocol," and "monitored sanitization-protocol target," and the like. However, the generalities should not be lost merely because of the nature of the examples.

Exemplary Deployment Overview

Turning to a first detailed example, FIG. 1 illustrates an exemplary deployment 100 of aspects, features, and embodiments of the present invention in a health care facility, such as a hospital 102, which is just one among many other facilities that can benefit from such a deployment. For the sake of simplicity, FIG. 1 shows hospital 102 as being abstracted to a plurality of health care areas 104(1) to 104(N), which, for the purposes of this disclosure, are any areas where there are encounters between patients, here, MPs, and/or item(s) in the MPs' immediate surroundings, and health care workers, here, MWs, where there is a risk of the MW(s) transmitting hazardous matter during such interaction to the MPs or to others. Such encounters include, but are not limited to direct contact between an MW and an MP, and contact with and/or handling of bodily fluids, excretions, items that have come into contact, etc., among other things. Examples of health care areas include in-patient rooms, treatment rooms, operating rooms, imaging rooms, check-up rooms, and patient recreation/activity rooms, among others.

Each health care area 104(1) to 104(N) includes one or more sanitization verification stations (only one verification station 106(1) to 106(N) per health care area is shown for simplicity), which are described in much detail below. As will also be described below in detail is the fact that the association of at least one sanitization verification station 106(1) to 106(N) with a corresponding health care area 104(1) to 104(N) results in that area becoming a "monitored space" in which deployment 100 monitors MWs for compliance with the appropriate sanitation protocols. In this embodiment, each sanitization verification station 106(1) to 106(N) is in communication with a sanitization compliance data processing system 108 via one or more communications links, which are collectively represented by cloud 110.

Sanitization compliance data processing system 108 provides a number of functionalities that are part of deployment 100. Sanitization compliance data processing system 108 can be implemented in any one or more computing components, such as servers, that can be located onsite at hospital 102, remotely from the hospital, or a combination of these. Regarding a combination of local and remote components for sanitization compliance data processing system 108, in one example, the local component can be a local server 112 located at hospital, while the remote component can be one or more web servers 114 located at a remote facility, such as a server farm. Local and remote web servers 112 and 114 can communicate with one another via a communications network 116, which may include one or more global, wide-area, and local-area networks. Cloud 110, i.e., the communications links between sanitization verification stations 106(1) to 106(N) and sanitization compliance data processing system 108, can comprise any suitable local area network(s), which can include at least one wired component (e.g., wired Ethernet), at least one wireless component (e.g., a wireless router/network), and any logical combination of wired and wireless components. Those skilled in the art will readily recognize the wide variety of ways in which the communications links of cloud 110 can be implemented, such that detailed recitations and an exhaustive list is not necessary for those skilled in the art to understand the breadth of the present invention. The functionalities of sanitization compliance data processing system 108 are described below in detail following descriptions of other parts of deployment 100.

For convenience, only one health care area 104(3) is shown in any detail to illustrate basic principles and aspects of the present invention. With an understanding of the basics principles, features, and aspects of the present invention, those skilled in the art will readily be able to implement them in any of health care areas 104(1), 104(2), and 104(4) to 104(N), regardless of their nature. In this example, health care area 104(3) is a double-occupancy inpatient room outfitted for two MPs 118 and 120 each assigned to a corresponding bed 122 and 124. FIG. 1 also depicts first and second MP read-range bubbles 118A and 120A corresponding respectively to patients 118 and 120. As will be understood from reading this entire disclosure, MP read-range bubbles 118A and 120A are established by interaction of certain patient-identification devices 128A and 128B carried, worn, or otherwise associated with each of MPs 118 and 120 with a node device 130 carried, worn, or otherwise associated with MW 126. It is noted that while only a single MW 126 and only one corresponding node device 130 is shown, in a typical deployment every health care worker that interacts with at least one patient carries a node device that is the same as or similar to node device 130. Detailed examples of patient-identification devices 128A and 128B and node device 130 are presented below; however, immediately following is a description of various functionalities of these devices to provide an overview.

Each patient-identification device 128A and 128B identifies the presence of the corresponding MP 118 and 120 to any node device, in this example, node device 130. This identification of presence can be conditional, for example, only occur when the node device (e.g., node device 130) is in a certain operational mode and/or within a certain proximity, as described further below. This identification of presence can be performed in any of a variety of ways, such as using techniques, such as, but not limited to, RFID detection or RF communication, infrared detection or communication, visible light detection or communication, ultrasonic detection or communication, and optical detection or recognition. In robust deployments, the interaction between a node device, such as node device 130, and a patient-identification device, such as either of patient-identification devices 128A and 128B, not only identifies the presence of a patient, but also identifies the particular patient and/or other information that may be associated with the particular patient. In this connection, each patient-identification device can be encoded with and/or transmit a unique patient identifier and/or other information that is/are readable by each of the node devices.

The interaction of node device 130 with each of patient-identification devices 128A and 128B is typically some sort of wireless interaction using, for example, energy in the electromagnetic spectrum (such as radio frequency energy, infrared energy, visible light energy, etc.), ultrasonic energy, magnetic energy, etc., and this interaction is used to establish the corresponding respective MP read-range bubble 118A and 120A. As used herein and in the appended claims, an "MP read-range bubble," such as each of MP read-range bubbles 118A and 120A, is a defined region containing a corresponding MP, such as MP 118 and 120. The term "bubble" is used to denote the 3D dimensionality of the region. For example, if each patient-identification device 128A and 128B includes one or more passive RFID tags and node device 130 includes an RFID reader, each MP read-range bubble 118A and 118B would typically be largely spherical in the absence of any physical structures and/or body parts that interfere with signal strength between the RFID reader and the RFID tag at issue. Hence, MP read-range bubbles 118A and 118B are depicted as circles in the 2D drawing. As those skilled in the art will recognize, however, when signal interference is present and/or each patient-identification device 128A and 128B is designed to be directional, the shapes of read-range bubbles 118A and 118B would be non-spherical. It is noted that other read-range bubbles, denoted "RFID read-range bubbles" are described below in connection with FIG. 5. As will become apparent from reading that description, RFID read-range bubbles are related to MP read-range bubbles but are related to node devices, rather than MPs.

Each MP read-range bubble is typically sized to encompass the corresponding MP and include a reasonable surrounding space that is likely to contain potentially contaminated items associated with the MP and with which the MW is likely to come into contact with during performance of their work with the MP. Examples of such items include all sorts of medical equipment that an MP may use or may be used on the MP. As will be appreciated, since a read-range bubble is defined by interaction between a node device (e.g., node device 130) and a patient-identification device (e.g., either of patient-identification devices 128A and 128B) associated with a particular MP as described above, when the MP wears or otherwise carries the patient-identification device, the MP read-range bubble moves with the MP wherever the MP may go. As will be described below in great detail, the determination of whether or not a given node device, and hence corresponding MW, is within an MP read-range bubble is used in various decision-making steps.

Each MP read-range bubble can be defined in any of a variety of ways and typically has a predetermined size, and, in some cases, an MP read-range bubble can have multiple predetermined sizes. For example, in the context of an RFID system in which each patient-identification device 128A and 128B comprises an RFID tag and node device 130 comprises a corresponding RFID tag reader, the size of the corresponding MP read-range bubble 118A and 120A can be determined by the strength of the RFID system's signal. In this example, the presence of node device 130, and hence MW 126, within an MP read-range bubble, such as either of MP read-range bubbles 118A and 118B, is determined simply by the node device being close enough to the corresponding patient-identification device, such as either of patient-identification devices 128A and 128B, to be able to obtain the patient-identifying information on that patient-identification device. Depending on the operational mode of node device 130, certain actions are taken depending on whether the node device and MW 126 are located inside or outside an MP read-range bubble.

As another example, regardless of the technology that node device 130 uses to identify the existence of a patient-identification device, the size of the corresponding MP read-range bubble can be determined in another manner, such as using an ultrasonic ranging system, optical ranging system or RF-type ranging system, used to determine the distance from the node device to the patient-identification device or MP. In this example, the presence of node device 130, and hence MW 126, within an MP read-range bubble, such as either of MP read-range bubbles 118A and 118B, is determined simply by the node device comparing an actual distance measurement from its ranging system to a preset boundary distance selected to define the outer boundary of the MP read-range bubble. If the actual measurement is greater than the preset boundary distance, then node device 130 determines that it and MW 126 are not in the MP read-range bubble. However, if the actual measurement is less than (or equal to, in this example) the preset boundary distance, then node device 130 determines that it, and MW 126, are in the MP read-range bubble. Again, depending on the operational mode of node device 130, certain actions are taken depending on whether the node device and MW 126 are located inside or outside an MP read-range bubble.

A monitored space 126A is established by interaction of node device 130 with any of sanitization verification stations 106(1) to 106(N). Each sanitization verification station 106(1) to 106(N) is located purposefully proximate to a corresponding health care area 104(1) to 104(N) to allow the creation of a corresponding monitored space, such as monitored space 126A, which is a region in which health care workers are mandated to follow certain sanitization protocols, such as hand-sanitizing protocols, because of the likelihood that the health care worker(s) will have encounters with the patient(s) in that space. In the present example, the sanitization protocol is a hand-sanitization protocol that essentially tracks the recommended protocol described in the WHO document mentioned in the Background section above, i.e., "Guidelines to Hand Hygiene in Health Care." Briefly, that protocol recommends that health care workers sanitize their hands before 1) touching a patient and 2) performing a clean/aseptic procedure and after 1) touching a patient, 2) touching a patient's surroundings, and 3) after body fluid exposure risk. Since all of these sanitization events can be related to a particular patient, such as either patient 118 and 120, they can be related to the corresponding MP read-range bubble, such as either of MP read-range bubbles 118A and 120A.

Simply stated, the WHO-recommended protocol, in the context of deployment 100 of FIG. 1, can be boiled down to requiring a sanitizing event occur just prior to an encounter between an MW and an MP (hereinafter, an "MW/MP encounter") for either of the two reasons listed above (termed herein "pre-patient-encounter sanitizing event" or more generically "pre-sanitization-target-encounter sanitizing event") and just subsequent to the MW/MP encounter after the occurrence of any of the three events listed above (termed herein "post-patient-encounter sanitizing event" or more generically "post-sanitization-target-encounter sanitizing event"). Correspondingly, a "monitored space," such as monitored space 126A, is defined herein as a region designated for containing one or more MPs in which MW/MP encounters are likely to occur with frequency and in which a pre-patient-encounter sanitizing event and a post-patient-encounter sanitizing event should occur within certain time limits, i.e., just before an MW/MP encounter and just after such an encounter.

An important feature of a sanitization protocol monitoring/compliance deployment of the present disclosure, such as deployment 100, is not only the monitoring of MWs in their interactions with MPs in monitored spaces, but also the verification that the MWs have actually performed the desired pre- and post-patient-encounter sanitizing events. Consequently, in terms of deployment 100 of FIG. 1, each monitored space, such as monitored space 126A, is facilitated by a corresponding sanitization verification station 106(1) to 106(N), which is designed and configured to perform at least one sanitization verification/effectiveness test following a sanitizing event performed by the corresponding MW, such as MW 126.

In one embodiment, described more fully below, monitoring within a monitored space is typically instigated, or authorized, by the relevant sanitization verification 106(1) to 106(N) triggering the node device, for example, node device 130, of the corresponding MW to "open" a new electronic monitoring session during which the node device electronically records various information concerning any or all of various events that occur after the record has been opened, such as events that occur in connection with MW/MP encounters. Depending on the speed at which sanitization verification stations 106(1) to 106(N) obtains sanitization verification/effectiveness measurements and results, the triggering of node device 130 to open a monitoring session can, for example, be in response to the mere initiation or performance of a verification/effectiveness test (e.g., for sensors that are too slow for real-time effectiveness triggering) or in response to a determination that the results of one or more effectiveness tests meet one or more corresponding threshold requirements. Examples of events for which node device 130 can record information, include, but are not limited to, 1) establishment of wireless contact with a particular patient-identification device (via the patient-identification device's read-range bubble as touched on above) and/or corresponding deduction of the beginning of an MW/MP encounter, 2) loss of contact with a particular patient-identification device and/or corresponding deduction of the end of the MW/MP encounter, 3) reestablishment of contact with the particular patient-identification device, 4) contact with a second patient-identification device, 5) timing-out of a countdown timer, and 6) activation of an alert or dismissal of an alert (override, etc.) by the corresponding MW, among others.

After a monitoring session has been opened by the execution of a pre-patient(sanitization-target)-encounter sanitization event verification test on health care worker 126 by corresponding sanitization verification station 106(3) in this example, that monitoring session can be effectively closed as a function of the MW performing a post-MW/MP-encounter sanitizing event and causing sanitization verification station 106(3) to perform a second sanitization-verification/effectiveness test to test the effectiveness of the post-patient(sanitization-target)-encounter sanitization event. Similar to the opening of the monitoring session, the triggering of node device 130 to close the session can, for example, be in response to the mere initiation or performance of one or more effectiveness tests (e.g., for sensors that are too slow for real-time triggering) or in response to a determination that the results of the effectiveness test(s) meet one or more threshold requirements. A detailed example of the interaction of a sanitization verification station 106(1) to 106(N) with any node device of illustrated deployment 100, such as node device 130, is described below.

Once a sanitization verification station, such as sanitization verification station 106(3), has authorized a monitoring session and the corresponding node device, here node device 130, has opened the monitoring session, the corresponding MW, here MW 126, may proceed to enter an MW/MP encounter with an MP in the monitored space, in this example either MP 118 or 120. It is noted that if authorization does not occur for some reason, the MW may still proceed to an MW/MP encounter, but the MW will not be in an authorized state, and that fact will be discernable from the information recorded by deployment 100. During the monitoring session, the node device monitors and records various events that establish when a monitored MW/MP encounter starts and ends, as well as monitors and records the status of the MW's authorization or sanitization as a function of various time limits and contact with one or both of patient-identification devices 128A and 128B. A detailed example of the functioning of a node device of the present invention during monitoring sessions is described below in connection with FIG. 8.

Components of Exemplary Deployment

Sanitization Verification Systems

Each sanitization verification system of the present disclosure, such as any one of sanitization verification stations 106(1) to 106(N), is designed and configured to perform at least one sanitization verification/effectiveness tests on each MW to verify that the MW has undergone the appropriate sanitization (such as a sanitizing of hands with an alcohol-based sanitizer) and/or measure the effectiveness of the sanitizing event performed by or on the MW. In the context of sanitization protocol monitoring/compliance system deployment 100 of FIG. 1 in which the MWs, such as MW 126, are directed to follow the hand-sanitization protocols recommended by the WHO, each sanitization verification station 106(1) to 106(N) is designed and configured to perform at least one hand-sanitization verification/effectiveness test on each MW after that MW has performed a hand-sanitizing procedure. The type of test(s) performed will vary as a function of the type of hand-sanitizing procedure. For example, if the hand-sanitizing procedure utilizes an alcohol-based sanitizer, then a corresponding sanitization verification/effectiveness test could be one that senses the amount of alcohol that evaporates from either or both of the sanitizee's hands within a given amount of time following performance of the hand-sanitizing procedure. As another example, if the hand-sanitizing procedure utilizes a sanitizer that includes an invisible-light-activated marker, then a corresponding sanitization verification/effectiveness test could be one that senses the amount, intensity, etc., of the marker on one or both of the sanitizee's hands. In a further example, if the hand-sanitizing procedure involves neither alcohol nor any other sort of sanitizer marker, then a corresponding verification/effectiveness test may be one that senses the amount of bacteria and/or other foreign matter remaining on the sanitizee's hands. For example, technology exists for spectral-analysis identification of bacteria at stand-off distances using quantum-cascade lasers. See, for example, U.S. Pat. No. 7,623,234 to Puzey and titled "SYSTEM AND METHOD FOR DETECTING AND IDENTIFYING AN ANALYTE," which is incorporated herein by reference for its teachings of such. A detailed example of a sanitization verification station implementing an alcohol-based hand-sanitization verification/effectiveness test is described below.

An additional core functionality that a sanitization verification station of the present disclosure includes is the ability to communicate with each node device, such as node device 130 of FIG. 1. This communication can be one-way or two-way, depending on the configuration of the sanitization protocol monitoring/compliance system deployment. As mentioned above in the Overview section, one aspect of interaction between a sanitization verification station and a node device is the opening of a monitoring session as a function of the execution of one or more pre-patient-encounter sanitization verification/effectiveness tests and the closing of that session as a function of one or more post-patient-encounter sanitization verification/effectiveness tests. Consequently, basic functionality of a sanitization verification station is communicating triggering signals to node devices that signal the devices to open and close monitoring sessions. As those skilled in the art will recognize, this can be done in any of a variety of ways, such as by a analog signals or digitally encoded signals, which are preferably, but not necessarily, transmitted wirelessly using a suitable wireless communications technology, such as WI-FI™ technology, short- and very-short-range RF technology (e.g., BLUETOOTH® technology, ANT™ technology, etc.), light technology (e.g., infrared technology), and ultrasonic technology.

As mentioned above, at its most basic, communication between a sanitization verification station and a node device can be one way. In such a case, the node device would be designed and configured to store monitoring-session records and other data collected over a period of time (e.g., during a health care worker's work shift), for example, for uploading to a central database, such as a database stored in a sanitization compliance data processing system, such as sanitization compliance data processing system 108 of FIG. 1. While one-way communication is viable, in other deployments, such as sanitization protocol monitoring/compliance system deployment 100 of FIG. 1, two-way communication is utilized.

Before describing scenarios and implementations involving two-way communication between a sanitization verification station and a node device, it is noted that examples of different bases upon which a sanitization verification station can instantiate a monitoring session include, but are not limited to, 1) sensing of one or more of the MW's hands in a region designated for the testing and 2) determining that one or more measurements made during testing (e.g., concentration of alcohol, light intensity and/or coverage of a sanitizer marker, bacteria/foreign matter count or other quantification or identification, etc.) is greater (or less than, depending on the type of indicator measured) a pre-determined threshold value that provides a defining line between acceptable (pass) and not acceptable (fail).

Regarding the former basis, this basis can be used for sanitization testing procedures that may not be able to render measurement results in a timely manner, for example, due to limitations of the technology used to implement a particular test or set of tests or complexity of the calculations to be performed. In such cases, the sanitization verification station can be set up to initiate the opening of a monitoring session without the measurement being finalized so as to not hold up progress of the MW. In this case, the measurement results are nonetheless eventually obtained. Once the measurement results have been obtained, they can be stored locally within the sanitization verification station and/or sent to another location, such as a sanitization compliance data processing system (e.g., system 108 of FIG. 1), for matching with the corresponding MW, sanitization verification station, monitored space, etc., for subsequent data analysis and reporting.

Regarding the latter basis for monitoring-session authorization, when a sanitization verification station can render measurement results quickly enough that the MW would not be unduly delayed, the sanitization protocol monitoring/compliance system deployment can be configured to use the measurement results to determine, in real time, whether or not the hands of the MW meet a minimum threshold sanitized level. As mentioned above, this can be done, for example, by the sanitization verification system comparing the measurement(s) to one or more acceptable-threshold values. If the measurement(s) indicate that the MW's hands have been acceptably sanitized, then, for example, the sanitization verification station may communicate an open-monitoring-session, or authorization, signal to the node device of the MW that causes the node device to open a new monitoring session if the sanitizing procedure just performed is a pre-MW/MP-encounter sanitizing procedure. The node device can additionally/alternatively use this signal for one or more other purposes, such as to initiate a timer and to cause an annunciator of the node device to provide an indication of the status. If the sanitizing procedure is a post-MW/MP-encounter sanitizing procedure, then, for example, the verification station may communicate a signal to the node device that causes the node device to control an annunciator to indicate that the health care worker performed the post-MW/PW-encounter sanitizing procedure successfully and that the worker's hands are properly sanitized. The node device may also use this signal to close the monitoring session and also, if the sanitization verification station and node device are so configured, to trigger the uploading of information collected by the node device during the monitoring session to the verification station.

On the other hand, if a comparison of the measurement(s) to one or more corresponding threshold values indicates that the level of sanitization of the MW's hands does not meet the requirements, then, for example, the sanitization verification station may still issue an open-monitoring-session signal if the sanitizing procedure is a pre-MW/PW-encounter sanitizing procedure. This way, interactions with one or more MPs would still be recorded. However, in addition to issuing an open-monitoring session signal, sanitization verification station could also be programmed to communicate a signal to node device that instructs the node device to alert the MW to the failed attempt at sanitizing his/her hands. While alert functionality of a node device is described in more detail below, briefly, alerts can take any suitable form, such as tactile (e.g., vibration), aural (e.g., beep(s) or other tone(s), spoken statement), visual (e.g., illumination of a red LED), etc., and any suitable combination of these. Additionally, or alternatively, the sanitization verification station itself may be outfitted with its own alert indicator(s). In conjunction with the issuance of an alert, the MW may be instructed to perform the sanitizing and/or verification/effectiveness testing procedures again.

It is noted that while in the foregoing example the sanitization verification station performed the task of determining whether or not the test measurement(s) indicated a successful sanitizing event, this functionality can be performed by another component of the sanitization protocol monitoring/compliance system deployment. For example, each node device can be programmed to receive the measurement data from the sanitization verification station, make the comparison with the preset threshold(s), and execute a next step according to the results of the comparison. Regarding the last item, the node device could be programmed, for example, to 1) open a monitoring session when the effectiveness results are for a pre-MW/MP-encounter sanitizing procedure and they are positive; 2) open a monitoring session but provide an alert to the MW when the effectiveness results are negative; and 3) communicate effectiveness results to the sanitization verification station, among others. In yet other sanitization protocol monitoring/compliance system deployments that include a sanitization compliance data processing system, such as sanitization compliance data processing system 108 of FIG. 1, the tasks of determining whether or not the test measurement(s) indicate(s) a successful sanitizing event and issuing notifications to a sanitization verification station and/or a corresponding node device can be performed by the sanitization compliance data processing system.

In some embodiments, each sanitization verification system can be designed and configured as a standalone station that can be installed in a patient room or other room or area of a health care facility, typically near a sanitizing station, i.e., a facility/place where an MW can perform a sanitizing procedure, such as a sanitizer dispensing station or a scrub sink. In lieu of a fixed sanitizing station, an MW could carry a personal sanitizer dispenser that dispenses a suitable hand sanitizer, such as an alcohol-based sanitizer. In other embodiments, each of some or all of the sanitizing verification stations may include an integrated hand-sanitizer station, such as a sanitizer dispenser. Those skilled in the art will readily understand the various ways in which a sanitization verification station of the present disclosure can be deployed based on the examples provided herein.

As mentioned above relative to FIG. 1, when a particular sanitization protocol monitoring/compliance system deployment, such as deployment 100, includes a sanitization compliance data processing system, each sanitization verification station can be in communication with the sanitization compliance data processing system so that it can provide data/singals to and/or receive data/signals from the sanitization compliance data processing system. Examples of data that a sanitization verification station can provide include, but are not limited to, a unique identifier identifying the specific verification station, measurement data and/or test result data from the verification/effectiveness test(s), a unique identifier identifying each MW that subjects his/her hands to a verification/effectiveness test at that verification station, and records and/or other data uploaded from any of the node devices, such as the monitoring session records mentioned above. Examples of data/signals that a sanitization verification station can receive include, but are not limited to, data and/or signals relating to calibration of the sanitization verification station and node status. Further details and examples of functionality that each sanitization verification station can be provided with are presented below.

As just mentioned, some of the data that a sanitization verification station of the present disclosure can provide to a sanitization compliance data processing system includes the verification station's own unique identifier and a unique identifier for each MW that initiates verification/effectiveness testing at that station. Each of these unique identifiers can be obtained and provided in any of a variety of ways. Regarding unique identifiers for sanitization verification stations, each verification station can, for example, be provided with an RFID tag and an RFID tag reader that can read its own RFID tag when prompted, for example, in conjunction with the initiation of the verification/effectiveness testing. This arrangement can be useful when implemented with RFID-tag-based equipment inventory systems, since the facility will already have experience with RFID-based systems and related software. Alternatively, each sanitization verification station can be programmed with a unique identifier that is stored in onboard memory and can be retrieved at an appropriate time, for example, in conjunction with the initiation of verification/effectiveness testing.

Regarding unique identifiers for MWs, each MW can be issued an identification badge, tag, or other item that includes a standoff-readable identification-bearing device, such as an RFID tag (typically of the passive type), that embodies a unique identifier associated with that MW. While RFID tags are ubiquitous and suitable choices for MW identification, those skilled in the art will readily appreciate that other types of identification technology, such as bar code, QR code, etc., could alternatively be used. Then, each sanitization verification station can be outfitted with a suitable standoff reader (e.g., RF-based, light-based, sound-based, etc.) that can read the MW's identification-bearing device. For example, when the MW's identification-bearing device is an RFID tag, the sanitization verification station can be outfitted with an RFID tag reader (which can be the same one mentioned above in the scenario wherein the sensing system has its own RFID tag) that reads the health care worker's RFID tag at an appropriate time, for example, in conjunction with initiation of verification/effectiveness testing. Alternatively, depending on how the node devices are configured, each node device may store the corresponding MW's unique identifier. Then, if/when the identifier is needed by a sanitization verification station, the sanitization verification station can be configured to query the node device for it. Alternatively, in some embodiments the sanitization protocol monitoring/compliance system deployment can be configured so that the node devices push the MW's unique identifier to each sanitization verification station with which the MW interacts.

In yet another example, each node device can be provided with one or more identification device readers, such as an RFID tag reader, which can read patient identification devices associated uniquely with corresponding respective MPs as well as MW identification devices and sanitization verification station identification devices, and can be configured to read those devices and provide the corresponding respective unique identifier data to a particular sanitization verification station at issue. Those skilled in the art will readily understand the variety of ways that unique identifying information can be obtained and handled using the examples herein as a guide.

Figure 2:
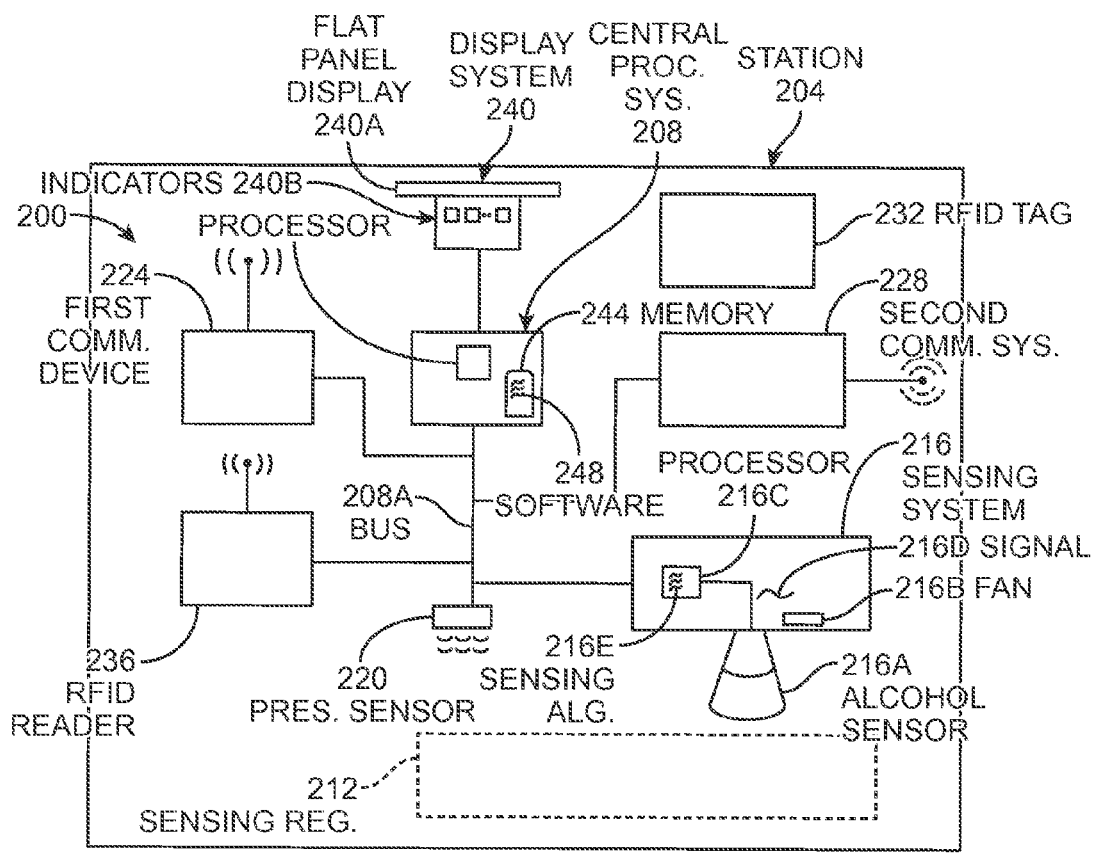
FIG. 2 is a schematic/block diagram of a unitary station embodying a sanitization verification system that can be used in a sanitization protocol monitoring/compliance system deployment of the present invention, such as the deployment of FIG. 1.

FIG. 2 illustrates an exemplary embodiment of a sanitization verification system 200 that can be used in a sanitization protocol monitoring/compliance system deployment of the present invention, such as deployment 100 of FIG. 1. Referring to FIG. 2, sanitization verification system 200 is embodied in a unitary verification station 204 that is designed and configured to perform a sanitization verification/effectiveness test for an alcohol-based sanitizer. Components of verification station 204 include a central processing system 208, a sensing region 212, an alcohol sensing/measurement system 216, a hand-presence sensor 220, a first communications system 224, a second communications system 228, an RFID tag 232, an RFID reader 236, and a display system 240, among other things. As is well known in the art, central processing system 208 may include one or more microprocessors or other processing devices (not shown), one or more memories (not shown), and one or more communications buses, such as bus 208A, or other input/output means. As will be readily appreciated, central processing system 208 is designed, configured, and programmed to provide at least the functionality of sanitization verification station 204 described above and below.

Sensing region 212 is a region where an MW places his/her hands for verification/effectiveness testing to be performed. Typically, especially in the present example with an alcohol-based sanitizer from which the alcohol therein evaporates relatively quickly, once an MW finishes sanitizing with a sanitizer (not shown) the MW relatively quickly (e.g., within about 3 seconds) moves his/her hands to sensing region 212 for verification/effectiveness testing by alcohol sensing/measurement system 216.

Alcohol sensing/measuring system 216 includes one or more suitable alcohol sensors 216A, such as one or more electronic noses that are sensitive to the presence of the alcohol(s) present in the subject sanitizer, such as isopropanol, ethanol, and n-propanol, among others, and any logical combination thereof. It is noted that if multiple sanitizer types are used in a particular health care setting, alcohol sensing/measuring system 216 can be configured to measure the presence of each type. In addition, it is noted that if the sensor technology used does not allow a just-used sensor to cleared and be ready for another sensing event in a relatively short amount of time, for example, the minimum amount of time that two MWs could successively sanitize and subject their hands to testing or that a single MW could re-sanitize after a failed sanitizing event, alcohol sensing/measuring system 216 may be provided with multiple sensors of the same type that are moved or otherwise individually placed into operation sequentially as needed for taking successive measurements. In one example, sensor 216A is 32 mm round alcohol-sensing electrochemical fuel cell sensor available from PAS Systems International, Fredericksburg, Va. Alcohol sensing/measurement system 216 may also include one or more fans 216B or other devices for moving alcohol vapors from sensing region 212 to sensor 216A to assist in the sensing/measurement process. In some embodiments, alcohol sensing/measurement system 216 may include its own processor 216C for converting the raw output of sensor 216A to a signal 216D suitable for providing to central processing system 208 and/or for converting the raw output of the sensor to a human meaningful value. In some embodiments, such value could be displayed to the health care worker, for example, via display 240.

In the embodiment shown in FIG. 2, hand-presence sensor 220 is provided so that sanitization compliance data processing system 208 knows when one or more hands are present in sensing region 212 and, therefore, knows when to activate alcohol sensing/measuring system 216. In one example, hand-presence sensor 220 is a GP2Y0D805Z0F infrared digital proximity sensor, available from Sharp Microelectronics of the Americas, Camas, Wash., but may be of any other suitable type. Activation of alcohol sensing/measuring system 216 can include, for example, any one or more of initiating execution of a sensing algorithm 216E within processor 216C, activating alcohol sensor 216A, and activating fan(s) 216B, among other things. In embodiments using multiple alcohol sensors due to relatively long sensor clearing times, hand-presence sensor 220 may also be used to trigger moving a fresh, or cleared, sensor into place when the hand-presence sensor detects that the hands have been removed from sensing region 212. Of course, such triggering can be accomplished in another manner, such as by using a timer or based on the operation of one or more fans.

First communications system 224 can be an RF or other type of wireless system for communicating information from sanitization verification station 204 to any node device of the present invention, such as node device 130 of FIG. 1 (see also node device 600 of FIG. 6), and/or information from any such node device to the verification station. For example, first communications system 224 can include at least one of a WI-FI™ device and a short- or very-short-range RF device, such as a BLUETOOTH® RF device, an ANT™ device, or the like. As described in the Overview section above, information handled by first communications system 224 can include, but not be limited to, sanitization verification pass (e.g., monitoring-session authorization) and fail signals, sanitization test data, sanitization verification station identification information, and information collected by node device during one or more monitoring sessions. In this example, first communications system 224 is in communication with sanitization compliance data processing system 208 via bus 208A, and the sanitization compliance data processing system controls the overall operation of sanitization verification station 204, including the operation of the first communications system.

Second communications system 228 can include any sort of device(s) that can communicate information from sanitization verification station 204 to a sanitization compliance data processing system, such as sanitization compliance data processing system 108 of FIG. 1 and/or from the sanitization compliance data processing system to the verification station. Second communications system 228 can include one or more wireless devices, such as IEEE 802.11 devices or equivalents, and/or one or more wired devices, such as IEEE 802.03 devices or equivalents, among others. As described in the Overview section above, information handled by second communications system 228 can include, but not be limited to, information concerning sanitization verification station 204, verification/effectiveness test data and related information collected at the verification station, and information collected by node devices that is uploaded to the verification station, including information collected during sanitization monitoring sessions. In this example, second communications system 228 is in communication with central processing system 208 via bus 208A, and the central processing system controls the operation of the second communications system.

RFID tag 232 is typically a passive-type RFID tag (though it can be of the active or battery assisted type) that contains an identifier that uniquely identifies sanitization verification station 204 so that usage and operation of the verification station can be tracked and associated with the user's (i.e., the MWs) of the station. RFID reader 236 includes circuitry and one or more antennas for reading RFID tag 232, if present, and any RFID tags (see below) uniquely associated with each MW as they approach to use verification station 204. RFID readers suitable for use as RFID reader 236 are ubiquitous and need not be described herein in further detail for those skilled in the art to make and use the present invention. In this example, RFID reader 236 is in communication with central processing system 208 via bus 208A, and the central processing system interacts with the RFID reader as needed. In lieu of RFID tag 232 and/or RFID reader 236, a unique identifier for sanitization verification station 204 can be stored in memory 244 associated with central processing system 208. Memory 244 is represented generically in FIG. 2, and it can contain any type of memory used in digital processing systems, including, but not limited to volatile (e.g., RAM, cache, etc.) and non-volatile memory (solid state storage memory, optical memory, magnetic memory, etc.), and any combination thereof.

Display system 240 can include any means suitable for conveying information to a person, such as an MW, proximate to sanitization verification station 204 and/or for allowing a user to interact with the verification station, such as to program it with desired settings and to control the various functionality it provides. Such information can include, but not be limited to, verification/effectiveness testing status and/or results, general status information for sanitation verification station 204, verification station functionality controls and configuration information, and MW sanitation status, among other things. To convey such information, display system 240 may include an electronic display 240A, e.g., a flat-panel video display or other type of display and/or one or more indicators 240B, such as aural indicators that emit beep(s) and/or other tone(s), spoken statements, and visual indicators that emit light, and any suitable combination of such indicators. Those skilled in the art will readily appreciate the variety of means that are available for implementing in display system 240 to provide the desired functionality of information conveying and/or receiving user input.

Central processing system 208 executes software instructions 248 (e.g., in firmware and/or other form(s)) that control all of the automated functionality and sequences of operation of sanitization verification station 204 as well as control the overall functioning of the verification station and its components. Those skilled in the art will readily be able to create software instructions 248 with routine programming knowledge once provided with a particular set of components and a particular set of functionalities, such as the functionalities described above and below.

Sanitization-Protocol-Target Identification Devices

Each sanitization-protocol-target identification device (e.g., patient-identification device in a health care context) can be any device that provides a corresponding sanitization-protocol target with an identifier that uniquely identifies the target and that can be read by a node device carried by an MW. In some embodiments in the health care context, each target-identification device is embodied in an identification bracelet that is generally similar to some types of conventional identification bracelets currently issued by hospitals and other health care facilities to patients but is configured to particularly enable certain functionality of a sanitation protocol monitoring/compliance system of the present disclosure. In non-health-care settings, as well as in health care settings, the sanitization-protocol-target identification devices can be embodied in forms other than bracelets, such as tags that can be affixed or otherwise attached to or carried by the corresponding target. Several examples of bracelet-based sanitization-protocol-target identification devices are described immediately below.

Generally, a sanitization protocol monitoring/compliance system of the present disclosure uses each sanitization-protocol-target identification device to identify the sanitization-protocol target, such as a patient, and to make various compliance and monitoring determinations and sanitization status updates relative to the sanitization-protocol target based on detection of a sanitization-protocol-target identification device. Such determinations and updates are based on proximity of a node device carried by an MW to a sanitization-protocol-target identification device. Close proximity of a node device to a sanitization-protocol-target identification device during a time when a monitoring session is open is the basis for inferring that there is an encounter between an MW and a sanitization-protocol target that warrants that the MW has properly sanitized. To effect this functionality, an MW/sanitization-target (e.g., MP) encounter region is defined and established around the sanitization-protocol target in which such an encounter is likely to occur. The encounter region can be defined in a number of ways, depending on how the sanitization protocol monitoring/compliance system is configured.

For example, if each node device is outfitted with an RFID reader and each sanitization-protocol-target identification device includes a passive RFID tag, then the MW/MP encounter region can be defined by the MP read-range bubble, which as mentioned above is the space bounded by an envelope that is spaced from the RFID tag in the sanitization-protocol-target identification device by a distance at which the read signal is just strong enough to allow the RFID reader of the node to detect the RFID tag. Correspondingly, the read signal strength within the MP read-range bubble is strong enough for RFID-tag detection and too weak outside the MP read-range bubble for RFID-tag detection. In this example, the size of the MW/MP encounter region is determined by the strength of the read signal. As another example, when read-signal strength is not considered, the encounter region can be determined by a combination of target-sanitization-identification device detection with some sort of distance-detection means, such as an ultrasonic distance detector or light-based distance detector, among others. In this example, the size of the MW/MP encounter region is determined by pre-establishing an envelope based on offset distance(s) (there could be multiple distances at different locations around the target) from the sanitization-protocol target or other reference within the encounter region. During operation, presence of an MW inside or outside an MP encounter region is determined by comparing an actual measured distance with the relevant pre-established offset distance. If the measured distance is less than the offset distance, the sanitization protocol monitoring/compliance system (.e.g., node device) would determine that the MW is inside the encounter region, and if the measured distance is greater than the offset distance, the sanitization protocol monitoring/compliance system (.e.g., node device) would determine that the MW is outside the encounter region.

Figure 3A:
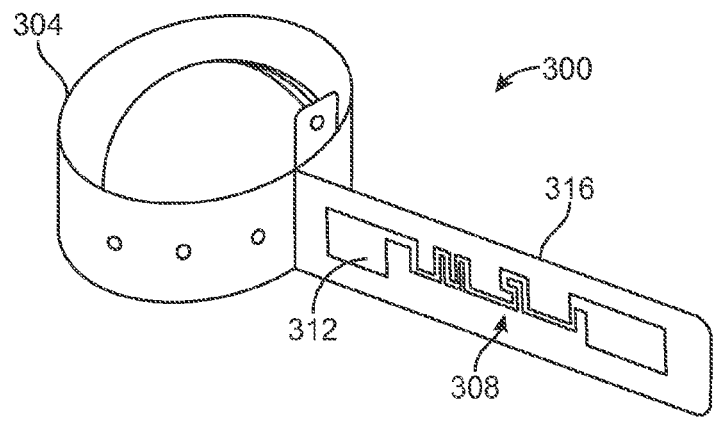
FIG. 3A is an isometric view of a sanitization-protocol-target identification device that can be used in a sanitization protocol monitoring/compliance system deployment of the present invention, such as the deployment of FIG. 1, wherein the device has a single radio-frequency identification (RFID) tag.

FIG. 3A illustrates one example of a sanitization-protocol-target identification device in the form of a band-type (e.g., bracelet- or anklet-type) patient-identification device 300 for a health care deployment of a sanitation protocol monitoring/compliance system of the present disclosure. Patient-identification device includes a band 304 and one or more passive RFID integrated circuits (ICs), here, one IC 308 having one antenna 312. Band 304 can be any suitable configuration and can be made of any suitable material in molded, sheet, spunbonded, woven, or other form, and any combination thereof. Typically, though not necessarily, band 304 would be made of a disposable material and would be configured in a manner that conforms to or adheres to a part of a patient's body, such as a wrist, arm, or ankle, and that may allow human and/or machine-readable printing to be placed on it.

Device 300 includes an appendage 316 that extends away from band 304 for supporting RFID tag 308 in a manner that increases the likelihood that antenna 312 is relatively free from structures, for example, body parts, that might interfere with the RFID tag being detected by an RFID reader. Appendage 316 can be made of the same material as band 304 and is preferably made of a material that minimizes absorbance and blocking of signals necessary for reading RFID tag 308. RFID tag 308 is secured to appendage 316 in any suitable manner, such as by adhesive bonding. RFID tag 308 can be encoded with unique patient identification information at an appropriate time, such as upon admission to the health care facility and may be printed upon and/or color coded to convey as much information visually as deemed appropriate or as desired for the particular facility. In the embodiment shown, RFID tag 308 is secured to an appendage 304A of band 304. This is done to lessen the likelihood of interference with the reading of RFID tag 308 by a node device (not shown) or other device having a compatible RFID reader. Any information stored on RFID tag 308, or portion thereof, can be encrypted to inhibit unauthorized access to that information.

Figure 3B:
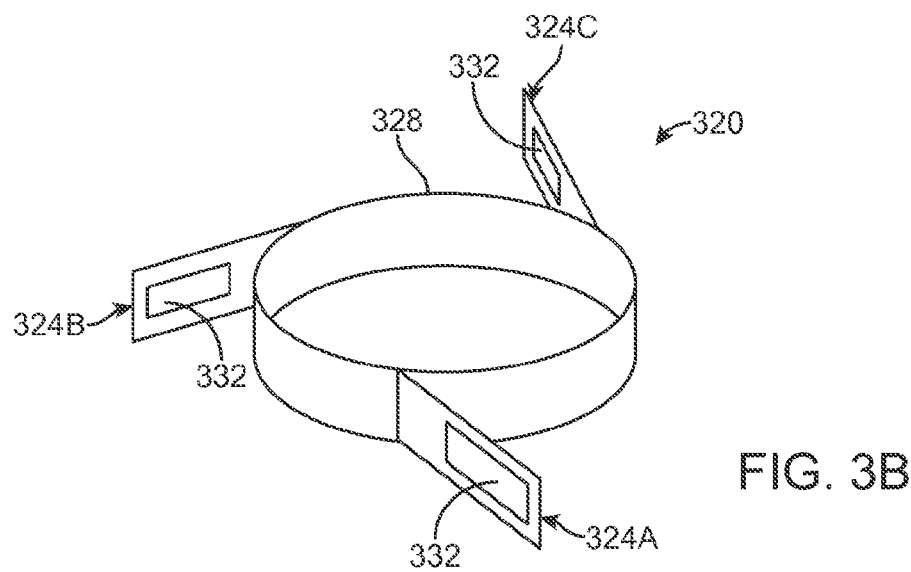
FIG. 3B is an isometric view of an alternative sanitization-protocol-target identification device that can be used in a sanitization protocol monitoring/compliance system deployment of the present invention, such as the deployment of FIG. 1, wherein the device has multiple RFID tags.

FIG. 3B illustrate another sanitization-protocol-target identification device 320 that is similar to device 300 of FIG. 3A in that it is embodied in a band form. However, instead of device 320 of FIG. 3B having a single appendage as in device 300 of FIG. 3A, device 320 of FIG. 3B has multiple such appendages, here three appendages 324A, 324B, and 324C, spaced apart around the circumference of the band 328. Each appendage 324A, 324B, and 324C includes one or more antenna modules 332; the spacing of the appendages increases the likelihood that if one (or more) of the RFID ICs is (are) occluded by a signal absorber, at least one of the remaining antenna modules is not critically occluded. This increase the likelihood that the size and shape of the read-range bubble is as close to desired size and shape as practicable.

Figure 3C:
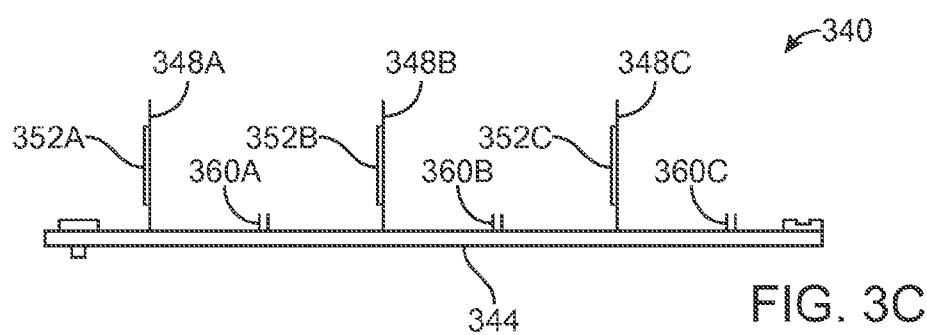
FIG. 3C is a side view of another sanitization-protocol-target identification device that can be used in a sanitization protocol monitoring/compliance system deployment of the present invention, such as the deployment of FIG. 1, showing the device in a pre-deployment configuration.
Figure 3D:
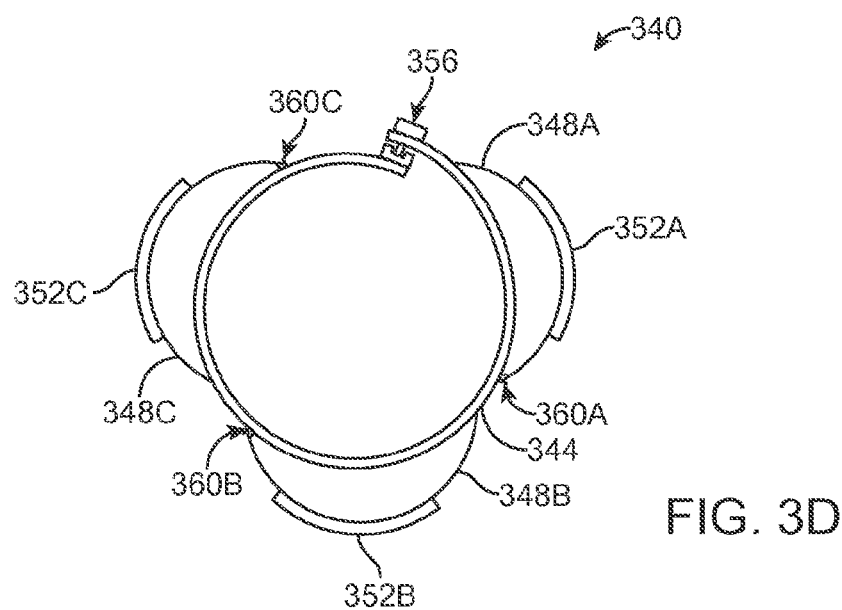
FIG. 3D is a top view of the sanitization-protocol-target identification device of FIG. 3C, showing the device in a deployment configuration with arch-shaped RFID tag standoff supports.

FIGS. 3C and 3D illustrate yet another example of a band-based sanitization-protocol-target identification device 340 that can be used in a sanitization protocol monitoring/compliance system of the present disclosure. Device 340 of FIG. 3C includes a band 344 and a plurality of tag standoff supports, here, three supports 348A, 348B, and 348C, that each contain a corresponding respective RFID tag 352A, 352B, and 253C. FIG. 3C shows band 344 in a flat, unconnected configuration and each of tag standoff supports 348A, 348B, and 348C also in an unconnected configuration. However, band 344 includes a closure mechanism 356 for holding band 344 in a ring shape. The band 344 also includes three connectors 360A, 360B, and 360C used for connecting the free ends (FIG. 3C) of corresponding respective ones of tag standoff supports 348A, 348B, and 348C to the band. Connectors 360A, 360B, and 360C are located so that when the free ends of antenna standoff supports 348A, 348B, and 348C are connected thereto, as shown in FIG. 3D (which also shows closure mechanism 356 engaged), each antenna standoff support forms an arched shape. This shaping of standoff supports 348A, 348B, and 348C beneficially provides airspace over and under tags 352A, 352B, and 253C that allows for an improved RFID signal detection rate by exposing both sides of the antennas to in-air signals and providing a higher percentage of reading signals when read by an RFID reader. The performance of device 340 is further enhanced by the separation of tags 352A, 352B, and 253C from patient installation band 344. Since an RFID tag can be grounded by contact with a patient's body, thereby compromising the tag's ability to respond to a read signal, attaching tag standoff supports 348A, 348B, and 348C at an angle and creating an arch shape removes tags 352A, 352B, and 352C from physical contact with the wearers' body where the installation band 344 is placed, so as to avoid or at least lessen the grounding issue.

In some embodiments of sanitization-protocol-target identification device 340, each RFID tag 352A, 352B, and 352C can be encoded with the same information. However, in other embodiments, each of tags 352A, 352B, and 352C can be encoded so that at least some of the encoded information differs among the tags. For example, each of tags 352A, 352B, and 352C is encoded with the same unique tag identifier, but the identifier on each tag is appended with a linking sequence. In the present case in which sanitization-protocol-target identification device 340, each tag 352A, 352B, and 352C is encoded with a unique identifier, such as "AAABBB", that is the same on all the tags, but tag 352A has an appended linking identifier, such as "111", encoded on it, making the tag reading "AAABBB-link 111", tag 352B has its linking identifier written to it as "222", and tag 352C has its linking identifier written to it as "333".

Figure 4A:
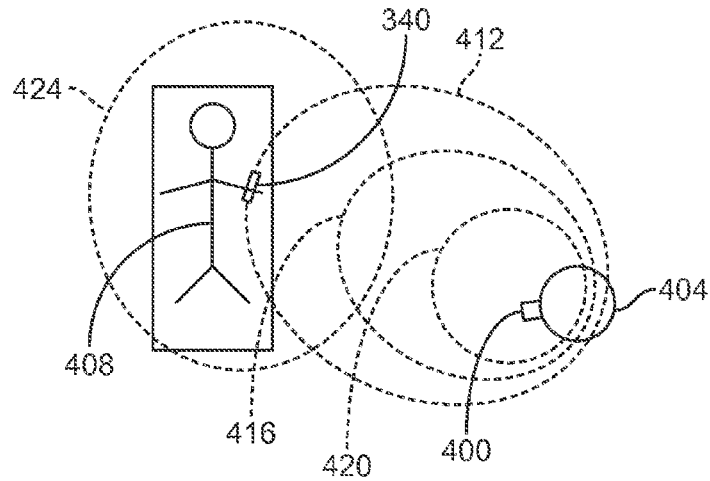
FIG. 4A is a schematic diagram illustrating an implementation of a sanitization-target-identification scheme in which each sanitization-protocol-target identification device includes three linked RFID tags and each node device has an RFID reader having multiple read ranges.

Referring to FIG. 4A, correspondingly each RFID-reader-containing node device worn by an MW, such as node device 400 worn by MW 404, has an RFID read range signal emitted in a bubble area in front of and/or around the MW, the shape of the bubble area dictated by a number of factors, such as the configuration antenna (not shown) of the node device, the presence of signal absorbers in the area, and signal characteristics of the RFID reader (not shown). When a sanitation verification station has issued authorization to node device 400 to open a monitoring session, firmware on the node device looks to establish contact with sanitization-protocol-target identification device 340, here worn by an MP 408, using a read formula of X number of identical reads reading unique identifiers, within Y time. The defined number X of identical unique hits in Y time to any one of tags 352A, 352B, and 352C (FIGS. 3C and 3D) establishes a positive link to sanitization-protocol-target identification device 340. The firmware aboard node device 400, recognizing a positive link to device 340, instructs the node device to maintain this link and to exclude other possible links from casual reads of other RFID tags that might be in the immediate vicinity of the node device, such as RFID tags on sanitization verification stations and RFID tags on other sanitization-protocol-target identification devices. To assist in doing this, the firmware, with node device 400 set to a relatively high RFID-reading-signal power (corresponding to read-range bubble 412 of FIG. 4A), looks for a linked RFID tag once the hit quantity X in the specified time Y qualifier has been established. It is noted that this initial relatively high RFID-reading-signal power can be set in response to node device 400 receiving the authorization from the sanitization verification station. Finding a pair of linked unique identifiers, such as the "AAABBB-link 111" and "AAABBB-link 333" identifier of RFID tags 352A and 352B (FIGS. 3C and 3D), respectively, node device 400 shrinks read-range bubble 412 of its reading signal to a smaller read-range bubble 416, for example, by reducing the power of its read signal. The firmware then looks for the last linked RFID tag, here RFID tag 352C (FIGS. 3C and 3D), and upon finding it via its unique linked identifier "AAABBB-link 222", it causes node device 400 to further reduce its RFID read-range bubble from read-range bubble 416 to a smaller read-range bubble 420 that is fairly tight around sanitization-protocol-target identification device 340 and MP 408. As those skilled in the art will readily appreciate, the size of the MW/MP encounter region 424 at read-range bubble 420 will be a function of the smallest read-range bubble 420. The read-range bubble of node device 400 is adjusted to large, medium, and small read range areas as long as the required number of hits X in the defined time Y defined is maintained. The plurality of linked tags 352A, 352B, and 352C (FIGS. 3C and 3D) increases the number of hits in the specified time, and the firmware does not allow a new association with a different unique identifier until a total break from the established association is achieved and a time clock has expired. On the other hand, if the hit rate for an identified target goes down, the RFID-signal-reading power can be increased to change the size of the read-range bubble, for example, from read-range bubble 420 to read-range bubble 416 or 412.

Figure 4B:
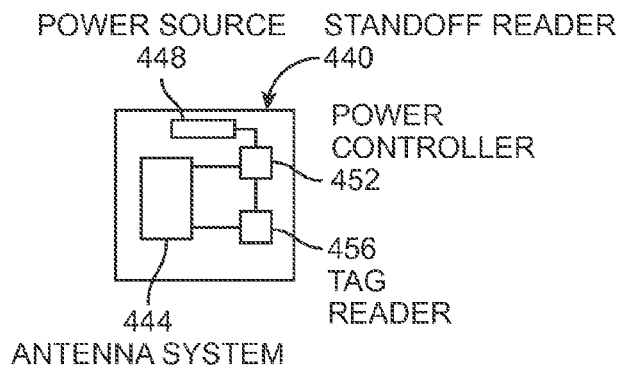
FIG. 4B is a high-level block diagram of an exemplary standoff RFID reader capable of reading the identification device of FIG. 4A.

FIG. 4B illustrates an exemplary standoff RFID tag reader 440 that is designed and configured for reading the plurality of linked tags 352A, 352B, and 352C of sanitization-protocol-target identification device 340 of FIGS. 3C, 3D, and 4A and provide a plurality of read-range bubbles of differing size, for example, bubbles 412, 416, and 420 of FIG. 4A. In this connection, exemplary standoff RFID tag reader 440 can be incorporated into node device 400 of FIG. 4A or any other suitable device. Referring to FIG. 4B, and also to FIGS. 4A and 3D as noted, in this example each of the plurality of linked tags 352A, 352B, and 352C (FIG. 3D) is a passive RFID tag that is energized and activated by power transmitted by one or more tag-energizing antennas tuned to the appropriate energizing frequency of the linked tags. In this example, standoff reader 440 includes an energizing antenna system 444 that is tuned to the energizing excitation frequency of linked RFID tags 352A, 352B, and 352C (FIG. 3D). Energizing antenna system 444 may include one or more individual tuned antennas (not shown). Power for energizing the antenna(s) of antenna system 444 is provided by a suitable power source 448 that may include a battery (not shown) and any electronics (not shown) needed to provide the appropriate output for energizing the antenna system. RFID tag energizing antennas and power electronics for providing power to such antennas are well known in the art.

In this example, the multiple differing-size read-range bubbles 412, 416, and 420 (FIG. 4A) are provided by changing the amount of power from power source 448 provided to antenna system 444 as a function of the number of linked RFID tags 352A, 352B, and 352C (FIG. 3D) standoff RFID reader 440 is detecting concurrently, as enabled, for example, by the linked-identifier scheme described above. In the embodiment of standoff RFID reader 440 shown, this changing of the power provided to antenna system 444 is performed by a power controller 452 that itself is under the control of a tag reader 546. As described above relative to FIG. 4A, the greater the number of linked tags 352A, 352B, and 352C (FIG. 3D) being detected concurrently, the smaller the read-range bubble that is provided by node device (FIG. 4A). In standoff RFID reader 440 of FIG. 4B, tag reader 456 provides the functionality of determining how many of linked tags 352A, 352B, and 352C (FIG. 3D) are being detected at any given time, or in a very small window of time, depending on exactly how the RFID-tag reading circuitry is configured. Tag reader 456 may then provide the number of concurrently detected linked tags 352A, 352B, and 352C (FIG. 3D) to power controller 452, which uses this number to determine which of multiple available power levels, here three power levels (high, intermediate, and low) corresponding respectively to read-range bubbles 412, 416, and 420 of FIG. 4A, it should provide to antenna system 444.

In one example, if tag reader 456 is detecting only a single one of linked tags 352A, 352B, and 352C (FIG. 3D) (or none of the linked tags) and the multiple-read-range bubble scheme calls for the largest read-range bubble (e.g., bubble 412 of FIG. 4A) when no or only one linked tag is detected, then the tag reader may provide power controller 452 a "0" of "1", or a binary equivalent, etc., and the power controller, as a result, would provide the maximum power to antenna system 444. However, when tag reader 456 is detecting all three linked tags 352A, 352B, and 352C (FIG. 3D) substantially concurrently and the scheme calls for a minimum-size read-range bubble (e.g., bubble 420 of FIG. 4A) under this condition, then the tag reader provides a "3" (or its binary equivalent, etc.) to power controller 452, and the power controller provides the lowest tag-energizing power to antenna system 444. Similarly, when tag reader 456 is detecting two of the three linked tags 352A, 352B, and 352C (FIG. 3D) substantially concurrently under the present scheme, then the tag reader provides a "2" (or its binary equivalent, etc.) to power controller 452, and the power controller provides an intermediate tag-energizing power to antenna system 444 to provide an intermediate-size read-range bubble (e.g., bubble 416 of FIG. 4A).

Those skilled in the art will recognize that standoff RFID reader 440 is a simple example of how a suitable multiple-read-range standoff reader can be configured and that many other configurations are possible, not only with RFID technology but other standoff technologies, as well. Consequently, it should be understood that exemplary standoff RFID reader 440 has been provided to simply illustrate the broad concepts attendant multiple-read-range standoff readers of the present invention and that this simple example should not be considered limiting the scope of the invention.

As those skilled in the art will readily appreciate, any of the foregoing bracelet-based designs and/or portions thereof can be embodied in a non-bracelet-based sanitization-protocol-target identification device using knowledge common in the art. Examples of non-bracelet-based sanitization-protocol-target identification devices include, but are not limited to, adhesive tags, hang tags, surgically embedded tags, badges, and other configuration wherein the linked tags are supported by a suitable support structure that can be associated in close proximity to the sanitization-protocol target. In addition, it is noted that the feature of multiple transponders or signaling devices and the ranging features described above can similarly be extended to other technologies, such as acoustic, optical, etc., mentioned above.

Node Devices and Monitored Worker Identification

Each node device in a sanitization protocol monitoring/compliance system of the present disclosure, such as node device 130 of system 100 of FIG. 1, can be configured to provide a variety of functionalities, many of which are described above in the Overview section. These functionalities on node device 130 can include, but are not limited to, 1) opening and closing monitoring sessions in response to interaction with sanitization verification stations, 2) recording various information during monitoring sessions relating to sanitization statuses and encounters with monitored sanitation-protocol targets (e.g., MPs), 3) providing indications of sanitization protocol adherence status of the MW carrying the node device, 4) interacting with sanitization verification stations, including receiving information therefrom and uploading information thereto, 5) recognizing sanitization-protocol-target identification devices and making decisions concerning the existence of MW/MP encounters, and 6) recognizing sanitization verification station identification devices and MW identification devices. Each of these functionalities is described in detail below.

A node device of the present disclosure is a mobile device that can be a dedicated device that is specially made of a particular sanitization protocol monitoring/compliance system of the present disclosure, or it can be a conventional mobile device that can be adapted to provide the requisite functionality. An example of such a conventional device is a smartphone, and those skilled in the art will readily recognize that most, or even all, of the functionalities described herein for a node device can be implemented in even today's smartphones using appropriate software, which can be provided in the form of a mobile-device software application. While conventional devices can be used, the following descriptions focus on dedicated devices. However, those skilled in the art will readily recognize how to program a conventional device so that it provides the requisite functionality for implementation in a sanitization protocol monitoring/compliance system of the present disclosure.

In one example, node device is a generic device, meaning that a worker can use any one of a plurality of like generic node devices, and that device will provide the requisite functionality. It will be appreciated that in other examples node devices can be permanently assigned corresponding respective workers and can be uniquely programmed accordingly, for example, to contain worker-specific information. However, this disclosure will use the generic configuration as a primary example.

Figure 5:
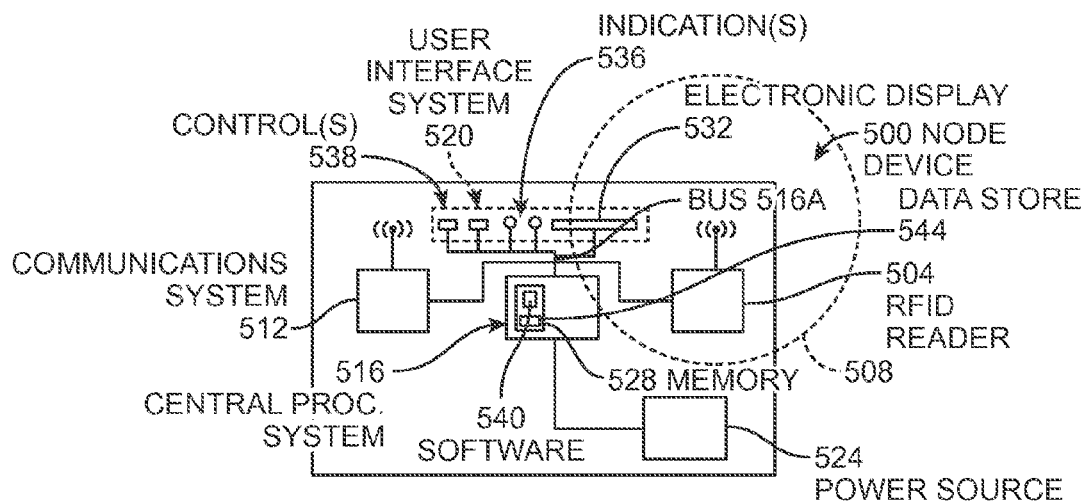
FIG. 5 is a schematic/block diagram of a node device that can be used in a sanitization protocol monitoring/compliance system deployment of the present invention.

FIG. 5 illustrates an exemplary node device 500 that can be used, for example, as node device 130 of FIG. 1 and any one of node devices 604(1) to 604(5) of FIG. 6, described below. In this example, node device 500 is described in the context of a sanitization protocol monitoring/compliance system in which each MW has an RFID tag encoded with a unique worker identifier, each sanitization verification station has an RFID tag encoded with a unique station identifier, and each monitored sanitization protocol target (e.g., MP) has an RFID tag encoded with a unique target identifier. Consequently, node device 500 includes an RFID reader 504 that is capable of reading the unique identifiers encoded into the various RFID tags just mentioned. In some embodiments, RFID reader 504 is designed and configured to limit its read-range bubble 508 to one or more predetermined sizes, such as in the manner described above in connection with FIG. 4, that are particularly suited to the deployment of the corresponding sanitization protocol monitoring/compliance system of which node device 500 is a part. As discussed above, the size(s) of read-range bubble 508 is directly correlated to the size of the MW/MP encounter region. Limiting the size of read-range bubble 508 also minimizes the number of RFID devices that node device 500 must interact with at any given time. As those skilled in the art will readily appreciate, in alternative embodiments RFID reader 504 may be replaced with one or more other types of readers, depending on the technology used to store the various unique identifiers.

In this example, node device 500 also includes a communications system 512, a central processing system 516, a user interface system 520, and a power source 524, which would typically be rechargeable, such as a rechargeable vibrating battery that can provide not only power for the node device, but also any vibratory annunciation functionality provided to the node device. Communications system 512 can be, for example, an RF or other type of wireless system for communicating information onboard node device 500 to any sanitization verification station (not shown) of the present invention that uses compatible communications technology, such as any of sanitization verification stations 106(1) to 106(N) of FIG. 1 and/or information from any such sanitization verification station to the node device. For example, communications system 512 can include at least one of a WI-FI™ device, a short- or very-short-range RF device, such as a BLUETOOTH® device, an ANT™ device, or the like. Other embodiments may include longer range RF devices, if desired, and may also, or alternatively include one or more wired ports for supporting any of various wired-communications protocols. As described above in the Overview section above, information transmitted/received by communications system 512 can include, but not be limited to, sanitization verification pass (e.g., monitoring-session authorization) and fail signals, sanitization test data, sanitization verification station identification information, equipment status, time synchronization, and information collected by node device during one or more monitoring sessions.

In this example, communications system 512 is in communication with central processing system 516 via a bus 516A, and the central processing system controls the overall operation of node device 500, including the operation of the communications system. It is noted that communications system 512 could be a wired system, but operation, such as continual docking or other structural connecting with a sanitization verification station, would likely be fairly cumbersome to users and cause mechanical wear on the docking/connecting parts. Therefore, wireless communications is typically preferred.

As is well known in the art, central processing system 516 may include one or more microprocessors or other digital processing devices (not shown), memory 528, and one or more communications buses, such as bus 516A, or other input/output means, among other components. As will be readily appreciated, central processing system 516 is designed, configured, and programmed to provide at least the functionality of node device 500 described herein. Memory 528 is represented generically in FIG. 5 any it can contain any type of memory used in digital processing systems, including, but not limited to, volatile (e.g., RAM, cache, etc.) and non-volatile memory (solid state storage memory, optical memory, magnetic memory, etc.), and any combination thereof.

User interface system 520 can include any means suitable for conveying information to a person, such as an MW, wearing, carrying, or otherwise proximate to node device 500 and/or for allowing a user to interact with the node device, such as to program it with desired settings and to control the various functionality it provides. Such information can include, but not be limited to, verification/effectiveness testing status and/or results, general status information from a sanitization verification station, node device functionality controls and configuration information, and MW sanitation status, among other things. To convey such information, user interface 520 may include an electronic display 532, e.g., a flat-panel video display or other type of display and/or one or more indicators 536, such as aural indicators that emit beep(s) and/or other tone(s), spoken statements, and visual indicators that emit light, and any suitable combination of such indicators, and one or more controls 538, for example, buttons, switches, knobs, or other controls for the MW to provide inputs, such as volume adjustments, alert cancellations, and the like. Those skilled in the art will readily appreciate the variety of means that are available for implementing in user interface 520 to provide the desired functionality of information conveying and/or receiving user input.

Power source 524 can include one or more batteries (not shown) or other source of electrical power, such as a fuel cell, for powering the various components of node device 500 during use, such as RFID reader 504, communications system 512, central processing system 516, and user interface system 520. Power source 524 can also include a charger (not shown) if the battery(ies) is/are of the rechargeable sort or a fuel supply if the power source requires fuel, such as in the case of a fuel cell. Those skilled in the art will understand how to implement any suitable electrical power source as power source 524.

Functionalities of node device 500 and various ones of its components are controlled by suitable software instructions 540 (e.g., in firmware and/or other form(s)) stored in memory 528 and executable by central processing system 516. Central processing system 516 executes software instructions 540 that control all of the automated functionality of node device 500 as well as control the overall functioning of the node device and its components. Those skilled in the art will readily be able to create software instructions 540 with routine programming knowledge once provided with a particular set of components and a particular set of functionalities, such as the functionalities described above and below.

A primary function of node device 500 is to collect a variety of information, including, but not limited to, 1) sanitization statuses of the MW carrying the node device, including time stamps, 2) MW/MP encounters the MW has with MPs during monitoring sessions, including MP identifiers and time stamps; 3) contacts the MW has with sanitization verification stations, including station identifiers and time stamps, 4) contacts the MW may have with MPs outside of a monitoring session, including MP identifiers and time stamps, 5) contacts the MW may have with other MWs, and 6) warnings and notifications given by the node device to the MW carrying the node, including types and time stamps. As described herein, a sanitization protocol monitoring/compliance system of the present disclosure can use this information to generate any of a variety of reports for assisting the facility or enterprise in monitoring protocol compliance, enforcing protocol, and/or educating MWs about protocol adherence, among other things.

Node device 500 can be designed and configured to store the foregoing and other information in a suitable database or other data store 544 contained in memory 528. As mentioned above, the information stored in data store 544 can be collected and stored therein for an entire shift until uploaded en mass, such as by a charging station. If done this way, once uploading is confirmed, node device 500 can be programmed to purge the data store. Alternatively, and as described below, some or all of the information stored in data store 544 can be uploaded and purged in a piecemeal fashion, such as in conjunction with sanitization verification events that occur at one or more sanitization verification stations before and after MW/MP encounters. This periodic uploading of data stored on node device 500 can be desirable since, from an overall system perspective, it gives the system nearly real-time performance.

Referring to FIG. 6, this figure shows a generic node device system 600 that includes a plurality of node devices, here five generic mobile node devices 604(1) to 604(5) and a charging station 608, which charges the node device when not in use. In addition to charging node devices 604(1) to 604(5), charging station 608 may be designed and configured to provide communications functionality the same as or similar to the communications functionality of a sanitization verification station, such as sanitization verification station 204 of FIG. 2, to allow the charging station to collect any monitoring session or other pertinent data stored in any of node devices 604(1) to 604(5) and that has not yet been uploaded to the central data processing system.

System 600 can be used as follows. When a worker starts a shift, she/he may take one of node devices 604(1) to 604(5) from charging station 608. In this example, each node device 604(1) to 604(5) has functionality described above relative to node device 500 of FIG. 5. System 600 of FIG. 6 can be set up so that when each node device 604(1) to 604(5) is docked with charging station 600 the node device is powered down or put into a special charging state. Then, when a worker 612 removes any of node devices 604(1) to 604(5) from charging station 608, such as node device 604(3), system 600 can be configured to turn on that node device or otherwise initiate a routine that sets the node device to a use state. For example, when worker 612 removes node device 604(3) from charging station 608, software 616 on the node device recognizes the removal, puts the node device into a use state, and causes the node device to look for a unique worker identifier 620 assigned to the worker by the institution or business utilizing the sanitization protocol monitoring/compliance system. In this example, unique worker identifier 620 is encoded into an RFID tag 624 worn or otherwise carried by worker 612. Upon finding the identifier, software 616 on node device 604(3) may record identifier 620 and the date and time, and set the node device to a use mode in which the node device is ready to provide its monitoring and other functionalities.

Typically, charging station 600 is located in a space where MW/MP encounters do not take place, such that as part of setting node device 604(3) to the use mode, software 616 may set an appropriate sanitization state indicator to "neutral" or similar state, indicating that the now-monitored worker has been recognized as being associated with the node device, but the sanitization state is neither "sanitized" nor "unsanitized", "authorized" nor "suspect", or any other states used in a particular deployment.

While in this example unique worker identifier 620 is encoded into RFID tag 624, in other embodiments the unique worker identifier can be encoded into another type of device, for example, an optical code, such as a bar code or QR code, among others. Alternatively to using encoded worker identifiers and identification devices, a generic node device and/or a charging station or other station can be configured to identify the worker in another manner, such as by fingerprint-scanning, photo-recognition of a face, hands, body, or other bio-identification technique. Once the worker is identified, a corresponding identifier can be stored in the node device for the duration of a user's workday, until the MW and node device are separated, etc.

Sanitization Compliance Data Processing System

Referring to FIG. 7, in an exemplary deployment, the sanitization compliance data processing system 700 (see also system 108 of FIG. 1) is implemented on one or more servers, such as server 704, that will typically be under control of the corresponding health care facility of the deployment, or a parent organization of the health care facility, or an outside service with which the health care facility or its parent contracts with to provide the deployment and its related services, among others. Whichever way sanitization compliance data processing system 700 is configured and instantiated, in this example each sanitization verification system 708(1) to 708(A) is in communication with the sanitization compliance data processing system 700 via a communications connection, here represented as a cloud 712 to cover all communications connections that may be utilized, including wired and wireless communications. The "initial" connection 716 of verification stations 708(1) to 708(A) can be either a wired communications connection (e.g., an Ethernet connection, among others) or a wireless communications connection (e.g., a WI-FIC® connection, among others), depending on the communications resources available at a particular location. Similar, each communications enabled charging station, here charging stations 720(1) to 720(B) (each of which has the functionality of charging station 608 of FIG. 6) has either a wired or wireless communication initial connection 716 to sanitization compliance data processing system 700, depending on the communications resources available at a particular location. Communications connections 712 and 716 allow information to be communicated between sanitization verification systems 708(1) to 708(A) and sanitization compliance data processing system 700 and information to be communicated between charging stations 720(1) to 720(B) and the sanitization compliance data processing system. As those skilled in the art will readily appreciate, wired and wireless communications connections suitable for use with the current deployment example are well known in the art, such that further details regarding them is not necessary for skilled artisans to understand and practice the present invention to its fullest scope.

As noted above, sanitization compliance data processing system 700 can provide a myriad of functionalities. For example, system 700 can be designed and configured to collect, in real or near-real time, maintain, archive, and safeguard information received from the patient registration system (not shown), sanitization verification stations 708(1) to 708(A), and charging stations 720(1) to 720(B). Such information can including, but not limited to, 1) sanitization verification testing data and 2) information concerning interactions between node devices (not shown) and MPs (not shown) and between node devices and MWs and between node devices and verification stations and charging stations, as provided by and/or relayed through verification stations and charging stations. System 700 can also be designed and configured to perform association of the collected data to, for example, correct time synchronization errors between various pieces of data collected and to attribute collected data to specific persons (MWs and/or MPs) and/or node devices and/or regions within the health care facility, etc. System 700 can further be designed and configured 1) to allow users to configure, manipulate, generate, etc., reports and/or alarms using such recorded information, 2) to make decisions on sanitization compliance, for example, by comparing verification test results with thresholds, record such decisions, 3) to communicate such decisions to node devices via verification stations, and/or 4) to manage the various components of the system and the various communications links among the components, among other things.

Any functionalities that sanitization compliance data processing system 700 provides can be effected by suitable software, which is shown generally by software 724 running on server 704. Those skilled in the art will readily appreciate that while software 724 is represented by a single box in FIG. 7, it may take any of a variety of forms. For example, software 724 may be implemented as a single set of machine-executable code, or it may be implemented as multiple code segments, or modules, that can be independently compiled as separate software applications that communicate with one another as appropriate. Those of ordinary skill in the software arts will readily understand how to implement any of the desired functionalities given a particular hardware/software architecture for implementing the deployment at issue. Because the variety of available architectures is vast and knowledge about how to program effectively in each of those architectures is well known, detailed explanations are not required for skilled artisans to implement the various aspects of software 724 in any known architecture.

Software 724 can be provided to and/or stored in server 704 as machine-executable instructions using any suitable machine-readable medium/media. In the context of this disclosure and the appended claims, the terms "machine-readable medium" and "machine-readable media" shall mean any type of device and devices designed and configured to store such software instructions. These terms do not include signals, such as carrier signals encoded with information in analog and/or digital format. It is noted, however, that software 724 can be provided to server using signals, for example, by transferring the software over the Internet. Practically speaking, however, even if transmitted by signals, at some point software 724 will be stored in machine-readable media, regardless of whether that media is deemed volatile or non-volatile, transitory or non-transitory, or not.

To store any of the information noted above and/or other information, sanitization compliance data processing system 700 includes a data store 728, which may be implemented in one or more memories (collectively represented by a single box 732), which can include any sort of memory designed and configured to provide such data storage. Software 724 can include any sort of machine-executable instructions for writing to data store 728 and reading from, manipulating, searching, etc. the information stored in the data store. As those skilled in the art will readily appreciate, the information stored in data store 728 can be manipulated using any suitable database management system, such as a relational database management system, among others.

Software 724 may also include one or more user interface (UI) applications or modules 736 that provide one or more UIs (not shown) to users via various sorts of computing devices, such as desktop computers 740(1) to 740(C), laptop/tablet computers/devices 744(1) to 744(D), and smartphones 748(1) to 748(E), among others. Such UIs can be, for example, application-based (e.g., run as a distinct application or module on the corresponding device) or can be browser-based (e.g., be presented to a user in a web browser running of the corresponding device. Those skilled in the art will readily understand the variety of ways to implement UIs depending on the type of device and the desired configuration and architecture of sanitization compliance data processing system 700. Software 724 can also be provided with suitable access protection to prevent/inhibit unauthorized access to information stored in data store 728.

Detailed Example of Operation of an Exemplary Deployment

Following is a detailed example of an exemplary deployment of a sanitization protocol monitoring/compliance system of the present disclosure. In this example, the setting for the deployment is a hospital in which the monitored spaces include patient rooms that each include a sanitization verification system embodied in a unitary verification station. Each verification station has an RFID tag that uniquely identifies that station and also has a hand detection sensor/system and an alcohol sensing system used to test for the presence of alcohol on hands presented to the verification station after they have been sanitized with an alcohol-based sanitizer. Each verification station also has a WI-FI™ module for wirelessly communicating with node devices and an RFID reader for reading its own RFID tag and RFID tags worn by hospital workers to uniquely identify them, especially MWs that each carry a generic node device made in accordance with the present invention. In addition, each verification station has a wired Ethernet connection to a sanitization compliance data processing system. Of course, and as described above, the connections between the verification stations and the sanitization compliance data processing system can be wireless in other embodiments.

Each node device in this example is a generic device designed to interact with verification stations in the deployment via a WI-FI™ module. Each node device's WI-FI™ module is also capable of communicating with a charging station that contains a compatible WI-FI™ module. Each generic node also has an RFID reader for reading hospital worker RFID tags and RFID tags on patient-identification bracelets that the hospital issues to patients as part of the admissions process to uniquely identify each patient. In this example, the RFID reader on each node has three read-power levels and, therefore, three read-range bubble sizes, and each identification bracelet has three linked RFID tags in the manner described above in connection with FIGS. 3B to 3D. Those skilled in the art will readily appreciate that the various components of this exemplary deployment, such as the node devices, RFID tags, sanitization verification stations, patient-identification bracelets, charging station, RFID reader, etc., and their subcomponents, may be the same as or similar to the like components depicted in FIGS. 1 to 6 and described in conjunction therewith above. However, for ease of readability, the following description avoids using element identifiers used above and in the drawings for these components and subcomponents. Those skilled in the art will readily be able to deduce the appropriate element identifiers and, therefore, be able to use the corresponding figures as references, if needed. With the foregoing configuration of the deployed sanitization protocol monitoring/compliance system, typical sequences of event are as follows.

Monitored Patients

A person enters the hospital to become an inpatient, and the hospital admits that person. As part of the admissions process, the hospital provides the person (hereinafter "MP" for "monitored patient") with an identification bracelet containing various information that is encrypted to inhibit unauthorized data collection and use. As mentioned, the bracelet contains three linked RFID tags that can be encoded as follows. In this example, the three RFID tags on the issued bracelet have the following corresponding respective serial numbers: 12345678, 12345679, and 12345680, and the linking code 678ABCDEFG is written to each, such that the tags are encoded, respectively, 12345678-678AB-CDEFG, 12345679-678ABCDEFG, and 12345680-678AB-CDEFG. Here, the sequence "678" is the linking code, and the "ABCDEFG" is institutional specific data written to the tags. The linking sequencing code links and identifies individual tags on the bracelet. At the time of admission and bracelet activation, the hospital also creates a file in the sanitization compliance data processing system that is associated with the bracelet serial numbers and linking code. As described below, by each bracelet containing a plurality of RFID tags, accuracy or reliability in establishing a relationship with node devices is increased.

The linking and sequencing code allows a node device to identify any one of the differing RFID tags on a single bracelet. This tag-linking scheme allows node firmware to cause actions to occur in the node device because one, two, or more linked tags are being read. As mentioned above, one action in particular is to change the tag read-range bubble size when multiple linked tags are being read. When the node device establishes an association (e.g., X reads of at least one RFID tag in Y time) with an identification bracelet, it begins looking for linking identifications. Upon reading two linked RFID tags (X reads in Y time) of the identification bracelet, the node device reduces the size of its read-range bubble by reducing the power of the read signal of its RFID reader to shrink the monitored region, or MW/MP encounter region, around the monitored person. Reading three linked RFID tags on the bracelet shrinks the node device's read-range bubble further by further reducing the strength of the read signal of the node device's RFID reader. Upon dropping contact with a linked RFID tag, the node device expands the read-range bubble to its next larger size by increasing the strength of the read signal of its RFID reader. Read-range bubble adjustments can be used for other purposes, too. For example, it may be desirable to have a small read-range bubble around an MW node device that is in the "neutral" state that expands when the node device is placed into an "authorized" state. Then, the enlarged read-range bubble stays large until the node device establishes contact with multiple linked RFID tags on a single identification bracelet, at which time the node device shrinks the read-range bubble as just described.

Monitored Workers

Every MW has a data file maintained by the sanitization compliance data processing system. Generally, the data in these files is accessible only by individuals having appropriate security clearance. Typically, when an MW begins employment with the hospital, the hospital issues the MW a permanent worker-badge that includes an RFID tag containing unique identification and other data concerning the MW, such as a personal identification string, an institution identification string, a job type (e.g., doctor, nurse, aide, etc.), an assigned ward or other workspace, among other things. The sanitization compliance data processing system can use these data categories for sorting, among other things. Some or all of this data is typically encrypted to prevent unauthorized reading.

Generic Node Device Initiation

To effect sanitization protocol monitoring/compliance, the hospital requires that all workers that interact with patients and/or items in a patient's immediate surroundings, such as medical equipment and devices, carry a node device of the present invention. As mentioned, in this example the node devices are generic, i.e., they are not assigned to any particular worker. As such, the overall use of a node device may proceed as follows. However, it is noted that in other embodiments node devices may be permanently assigned to corresponding workers. Those skilled in the art will readily understand the changes that can, and/or need to, be changed to implement permanently assigned devices.

At the beginning of her/his workday, an MW removes a generic node device from its charging station. The node device and/or charging station are configured so that the node device is automatically activated by the removal from the station. The node device maintains a running log of data and of its internal state changes. Firmware on the node device is designed and configured to instruct the node device as to what data is to be maintained and what data is to be discarded, depending on a variety of factors, including the state of the node and what the node is reading. Generally, this deployment utilizes two types of files. However, these file types are more a function of data matching at the sanitization compliance data processing system than they are a function of node operation.

As part of the activation, firmware on the node device instructs the node device to create an initiation file, which, once uploaded to the sanitization compliance data processing system, the sanitization compliance data processing system will recognize as the start of a monitoring period. At activation, the node device seeks to read the MW's RFID tag and stores information retrieved from that RFID tag upon a successfully reading. In response to a successful reading of the MW's RFID tag, the node device writes the data from the MW's tag, date, and time, to the initiation file. An initiation file is the first file of a monitoring period, for example, the worker's work day. It is noted that a monitoring period is different from a monitoring session, which is described above and below in detail. Only one initiation file per monitoring period is allowed by the node device's firmware. For a different or new MW association, the node device must be returned to the charging station and docked thereto, where any remaining files are downloaded and sent to the sanitization compliance data processing system and the node memory is cleared.

The node device's firmware ensures that the node device will maintain the association with the particular MW throughout a monitoring period. If contact is lost, the node device searches to reestablish this same relationship. If, after a predetermined period of time, contact is not reestablished, the node device issues a "no association" alarm and records the time when the loss was confirmed. If an initial association is not achieved in the prescribed period of time, the "no association" alarm is likewise activated and the event is recorded in a log file on the node device. Throughout a monitoring period, the node device's firmware uses the MW's RFID tag data to designate all files saved as data. It is noted that in this example, the node device has three primary action-causing states, "neutral," "suspect," and "authorized" and a quasi-state "suspect pending". State changes are written to the node device's internal data storage, and the events that follow for a prescribed time period (or until a prescribed event occurs) are likewise written to the onboard storage. When the node device's firmware recognizes the completion of a successful initiation association, it enters the "neutral" state. It is noted that while the node device's RFID reader is constantly searching for and reading RFID tag information, the device's firmware instructs the device to save or discard certain read data in accordance with predefined criteria, which is outside the scope of the present disclosure and is not needed for those skilled in the art to make and implement a sanitization protocol monitoring/compliance system or the present disclosure, or any part thereof.

Once the MW's node device has successfully associated with the MW and has switched to the neutral state, the node device is ready for use throughout the MW's workday, including establishing and recording data during monitoring sessions (described below) for MW/MP encounters in designated health care areas. At the end of the workday, the MW returns the node device to the charging station, where any non-uploaded collected-data files remaining on the device are uploaded to the sanitization compliance data processing system, along with the date and time of the docking and closing of the monitoring period.

Monitoring Sessions

Figure 8:
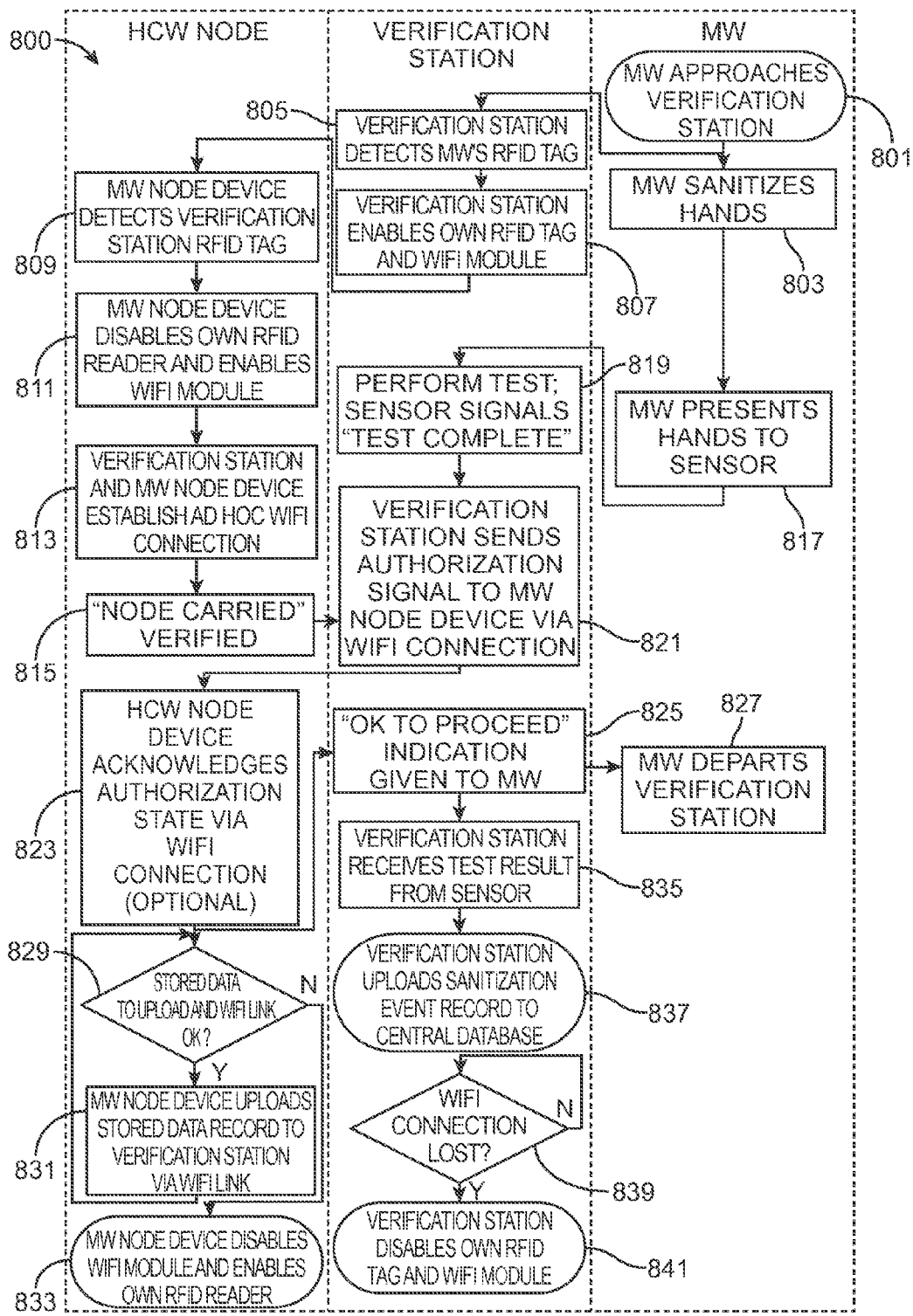
FIG. 8 is flow diagram illustrating an exemplary method of 1) establishing, in a health care setting, a monitoring session and 2) interacting with a sanitization verification station made in accordance with the present invention.

When the node device has been initiated and is in a monitored period, it is ready for use. FIG. 8 illustrates a method 800 of establishing a monitoring session within a monitored space in which health care workers are to follow the WHO hand-sanitization protocols mentioned above. As a reminder, under those protocols, health care workers, and especially MWs, are supposed to sanitize their hands just prior to an MW/MP encounter and just after such an encounter in that space. In this example, the monitored space is a patient room, and a single sanitization verification station is located in the room. While it should be apparent from the operation of the sanitization protocol monitoring/compliance system described herein, it is noted that it is not the overall space of the health care area that is monitored, but rather it is the MWs that are monitored by their various interactions with the sanitization verification station and the one or more MPs and/or MWs in the space.

At step 801 the MW approaches the sanitization verification station in the monitored space at issue where the MW is planning an MW/MP encounter. According to the sanitization protocol, at step 803 the MW sanitizes her/his hands, here with an alcohol-based sanitizer as mentioned above. Typically, the sanitizer dispenser is located proximate to or integrated into the sanitization verification station, such that the MW's RFID tag is within read-range of the RFID reader aboard the sanitization verification station. Consequently, at step 805 the sanitization verification station detects the MW's RFID tag. At step 807, the sanitization verification station enables its own RFID tag and WI-FI™ module for communicating with the MW's node device. At step 809, the RFID reader aboard MW's node device detects the RFID tag of the sanitization verification station. The MW's node device then disables its own RFID reader and enables its WI-FI™ module at step 811, and at step 813, the sanitization verification station and node device establish a mutual ad hoc WI-FI™ connection. At step 815, in response to establishing the WI-FI™ connection, the verification station establishes that the MW is indeed carrying a node and records a "node carried" indicator to its data store, along with a date, time, and verification station identification data.

At or around the same time steps 805 to 815 are being performed, at step 817 the MW presents her/his hands to the testing region of the sanitization verification station, which triggers the verification station to perform at step 819 a test that senses alcohol present on/evaporating from the MW's hands. As described above in connection with exemplary sanitization verification station 204 of FIG. 2, the triggering of the alcohol testing can be achieved with a suitable hand-presence sensor and the testing can be performed with one or more suitable alcohol sensors. When testing is complete, also at step 819 the alcohol testing system issues a "test complete" signal, and at step 821 the sanitization verification station sends an authorization signal to the MW's node device via the WI-FI™ connection. As mentioned above, the authorization signal does not need to be based on the achievement of any particular results from the alcohol testing. Rather, the signal can be based simply on the fact that the test was performed. Results can be matched up and dealt with later on in the sanitization compliance data processing system as desired.

At optional step 823, the node device acknowledges receipt of the authorization signal and places the node device into the authorized state. At step 825, the sanitization verification station provides an indication to the MW that she/he is authorized to proceed to initiate an MW/MP encounter based on a hand-sanitization event having been performed. This authorization also effectively starts a monitoring session within the node device. Again, in this embodiment positive test results are assumed for this authorization process. In other embodiments, authorization can be based on actual positive results, i.e., results that are determined in real time based on a comparison of sensor readings with a preset threshold value. The indication at step 825 can be aural or visual, such as a display of "OK TO PROCEED" on a flat panel display. At step 827, the MW departs from the sanitization verification station and proceeds to subject patient for an MW/MP encounter.

While the MW is still proximate to the sanitization verification station or even after the MW has moved away from the verification station, as long as the WI-FI™ connection between the MWs node device and the verification station is maintained, additional steps can occur. For example, at step 829 the node device and the sanitization verification station can determine whether or not there are any stored data on the node device that has not yet been uploaded to the sanitization compliance data processing system. If there is data present on the node device that has not yet been uploaded, at step 831 the node device uploads the stored data records to the sanitization verification station via the WI-FI™ connection. After the data uploading is complete, or if there was not any data aboard the node device to be uploaded, at step 833 the node device may disable its WI-FI™ module to reduce the power usage of the node device.

After the sanitization verification station has provided an indication for the MW to proceed at step 825, if the verification station is configured such that the alcohol test results are not used for the node authorization process, then at step 835 the alcohol testing system can provide the test results to the sanitization compliance data processing system of the verification system, which may store the results in memory, along with a date and time stamp and MW and verification station identification data to form a sanitization event record. At step 837, the sanitization verification station uploads the sanitization event record to the sanitization compliance data processing system via its Ethernet connection to the sanitization compliance data processing system. It is noted that at step 839 the sanitization verification station continually assesses whether the WI-FI™ connection with the node device is lost. If the WI-FI™ connection is lost, then at step 841 the sanitization verification station disables its WI-FI™ module.

MW/MP Encounters

At step 827 of method 800 of FIG. 8, the MW departed from the sanitization authorization station with her/his node device being authorized for a monitoring session. This step is also reflected in method 900 of FIG. 9 at step 901 at which the node device is authorized by the sanitization verification station to begin a monitoring session in the manner just describes relative to FIG. 8. Based on this authorization, at step 903 the node device 1) provides an indicator, such as a green indicator light, 2) increases the read-range bubble of its RFID reader by increasing the strength of its read signal, and 3) starts an initial-contact timer that provides a predetermined amount of time in which the MW must make initial contact with an MP or else the node device will change from an authorized state to a neutral state where the MW is not authorized to have an MW/MP encounter without re-sanitizing.

At step 905, the node device searches for contact with an MP by the node device's RFID reader continually polling for the presence of a patient's RFID tag. At step 907, the node device determines whether or not the RFID reader has established contact with a patient RFID tag. If the RFID reader has not established contact with a patient RFID tag, then the node device enters a loop 909 that includes checking, at step 911, whether or not the initial-contact timer has timed out or not. If the initial-contact timer has not timed out, then method 900 returns to step 905. However, if the node device determines at step 911 that the initial-contact timer has timed out, then at step 913 the node device changes its state to "suspect" and may provide one or more notifications (e.g., visual, tactile, audible, and any combination thereof) of the state change to the MW. When the state changes, the MW should be trained to know that she/he must re-sanitize and return to the, or any, sanitization verification station for another authorization, before the MW can again approach a patient for an MW/MP encounter. In addition, this state transition may be recorded, for example, in the node device and become part of the file uploaded to the sanitization compliance data processing system.

If at step 907 the node device determines that an initial contact with an MP's RFID tag has occurred, at step 915 the node device continues polling via its RFID reader to establish that firm contact with that RFID tag has occurred. In the context of the patient's bracelet including three linked tags, step 915 can include making contact with and identifying the linked tags and successively changing the size of the node device's read-range bubble, as described above. At step 917, the node device determines whether or not its RFID reader has made contact with all three linked RFID tags of a particular MP's identification bracelet. If so, method 900 proceeds to step 919 at which the node device assumes/ infers that the MW has initiated an MW/MP encounter and, therefore, stops the initial-contact timer. Also at step 919, the node device changes its state to "suspect pending," which is an interim state prior to the "suspect" state that is delayed by a lost-contact clock, as described below. The "suspect pending" state allows the node device's indicators to display an indication that a valid MW/MP encounter is in process. However, it also prevents the MW from visiting another MP that may be proximate to the MP of the initial MW/MP encounter while in an authorized state. With an MW/MP encounter identified, the node device enters a loop 921 at which the node device determines at step 923 whether or not its RFID reader, now in the lowest-power, smallest read-range bubble state, has lost contact with the MP's identification bracelet. If not, loop 921 continues, as the MW/MP encounter is presumed to continue.

However, if at step 923 the node device determines that previously established contact with the MP's identification bracelet has been lost, method 900 proceeds to step 925 at which the node device starts a lost-contact timer. This timer allows contact between the node device and the subject MP's identification bracelet to be lost for relatively short periods of time without requiring the MW to re-sanitize. In essence, as long as the lost-contact timer has not timed out, the current MW/MP encounter is presumed to be continuing. Consequently, at step 927 the node device determines whether or not the lost-contact timer has timed out. If not, at step 929 the node device determines whether or not contact between its RFID reader and the subject MP's identification bracelet has been restored. However, if the node device determines that the lost-contact timer has timed out, then at step 931 the node device changes its state to "suspect" and may provide one or more notifications (e.g., visual, tactile, audible, and any combination thereof) of the state change to the MW.

Returning to step 929, if the node device determines that contact between its RFID reader and the subject MP's identification bracelet has been restored, at step 933 the node device resets the temporary leave timer and returns to step 923 of continually monitoring the state of contact between the RFID reader and the identification bracelet. However, if contact with the subject MP's identification bracelet has not been restored at step 929, method 900 proceeds to step 935 wherein the node device determines whether or not its RFID reader has established contact with the identification bracelet of a different MP, i.e., an MP other than the one for which full contact was established at step 917. If the node device determines that such other contact has occurred, then at step 937 the node device changes its state to "suspect" and may provide one or more notifications (e.g., visual, tactile, audible, and any combination thereof) of the state change to the MW.

If at step 935 the node device determines that its RFID reader has not established contact with another MP's identification device, then method 900 continues to step 939 at which the node device determines whether or not the MW has performed an exit sanitizing and sanitization verification at the initial sanitization verification station or any other sanitization verification station that may be present within a distance the MW can traverse before the lost-contact timer times out. If the node device determines at step 939 that MW has performed a post-MW/MP-encounter sanitizing and the sanitizing has been verified, then at step 941 the node device stops the lost-contact timer and changes its state to "authorized" again. The detection of the performance and verification of a sanitizing event performed by the MW can be effected by a sanitization-verification signal received by the node device from a sanitization verification station. Such signal can be the same as the authorization signal from step 821 of method 800 of FIG. 8, and it can be obtained in the manner described in method 800. As described in connection with step 903 of method 900 of FIG. 9, the receiving by the node device of authorization based on the performance of a hand sanitization starts and initial-contact timer. Assuming that the verification station in this example is in a patient room, if the MW chooses to leave the room, the initial-contact timer will typically time out because the node device does not detect any patient identification devices. In response to the initial-contact timer timing out, the node device places itself into the "neutral" state. Once the node device is back in the "neutral" state, the MW can go about her/his duties, including implementing method 800 of FIG. 8 for another MW/MP encounter. Referring back to FIG. 9, if at step 939 the node device does not detect that an exit sanitizing has been verified, method 900 enters a loop 943 that continues until one of the decision steps 927, 929, 935, and 939 has an affirmative answer.

All of the preceding steps after decision step 917 answered in the affirmative deal with the node device's determinations and actions if the node device establishes firm contact with the MP identification bracelet initially encountered at step 907. However, if firm contact with that identification bracelet is not made at step 917, then method 900 proceeds to step 945 at which the node device determines whether or not its RFID reader still has contact with at least one of the linked RFID tags on the bracelet. If so, method 900 proceeds back to step 915 of trying to establish firm contact with the identification bracelet. However, if the node device determines at step 945 that contact between its RFID reader and at least one of the RFID tags on the identification bracelet of the initial contact of step 907 is lost, then method 900 loops back to loop 909.

Node Device States and Alarms

As mentioned above, in the present example four states/quasi-states are used for the node device. These states are "neutral," "authorized," "suspect," and "suspect pending." Following is an additional explanation of these states and their function within the health care sanitization protocol compliance/monitoring presented here in detail to illustrate aspects and features of the present invention. As can be deduced from the foregoing descriptions of methods 800 and 900, the neutral state will typically be the state that an MW's node device will be in much of the time. For example, whenever a health care worker is not currently involved in a valid MW/MP encounter, has performed an exit sanitization procedure following her/his most recent MW/MP encounter, and has experienced the initial-contact timer timing out, the node device places itself into the neutral state. The node device may display an indicator, for example, a yellow or other color light, etc., notifying the MW and/or others of its neutral state. In the present embodiment, each node device records all changes of state to neutral, along with a date/time stamp of when the state-change occurred.

The authorized state is described extensively above. However, to generalize, the authorized state is the state that a node device puts itself into in response to receiving an authorization signal from a sanitization verification station. In the present example, the authorized state is accompanied by the starting and running of an initial-contact timer that gives the MW a reasonable amount of time to enter into a valid MW/MP encounter, i.e., an MW/MP encounter in which the assumption is that the MW has been properly sanitized. If the initial-contact timer times-out before firm contact is established with an MP identification device, as described above in connection with step 913 of method 900 of FIG. 9 the node device changes its state to the neutral state.

However, if the MW's node device establishes firm contact with an MP identification device before the initial-contact timer times-out, then the node device changes its state to suspect pending. In one embodiment, the node device may display an indicator that it is in the suspect-pending state, which could otherwise be referred to as an "active MW/MP encounter state," a "valid MW/MP encounter state," or the like. The suspect-pending state is a quasi-state of sorts that in this example identifies that the MW is in an active, or valid, MW/MP encounter with a particular MP. The suspect-pending state works as a signal to the node device that if one of several events occur while the node device is in the suspect-pending state, then it should change to a suspect state. The suspect state is a state in which the node device issues an alarm to the MW to indicate that the MW is assumed to be violating the sanitization protocol being implemented by the sanitization protocol compliance/monitoring system and is no longer in a valid MW/MP encounter. The alarm may include the display of one or more haptic, visual, and audible indicators, such as a vibration, flashing light(s), audible alerts, or any combination of these.

Figure 9:
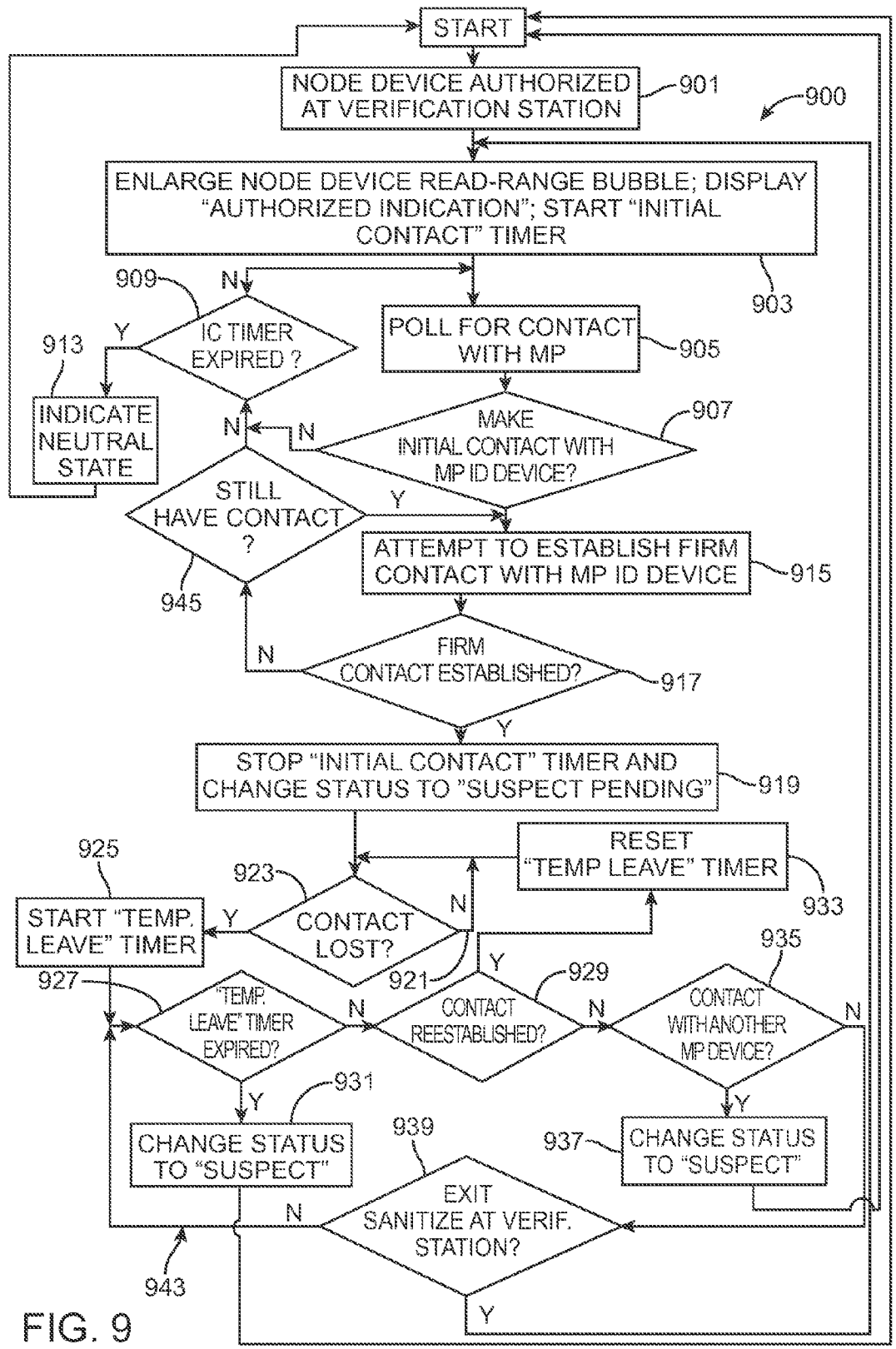
FIG. 9 is a flow diagram illustrating an exemplary method of establishing and ending a monitored encounter between a health care worker and a patient, wherein the health care worker carries a node device made in accordance with the present invention and the patient has an identification device made in accordance with the present invention.

As an example of the node device changing from the suspect-pending state to the suspect state, while in the suspect-pending state, when the node device has detected that the MW has moved outside the range of the MP identification device that caused the suspect-pending status, it starts the temporary leave timer (see step 925 of method 900 of FIG. 9). If the temporary leave timer times-out before the MW gets back into range of the original MP identification device or before the MW performs an "exit" sanitization at a sanitization verification station, then the node device changes its state from suspect-pending to suspect and issues an alarm indicating that the MW is no longer in a valid MW/MP state and is, effectively, assumed to be in an unsanitary state that is not in adherence with the sanitization protocol. As mentioned above, as an alarm the node device can display whichever indicator(s) it has be programmed to display, such as vibration, flashing light(s), audible warning, or any combination of these. At this point, the MW can act to cancel the alarm, for example, using a button or other feature on the node device itself or by re-sanitizing at a sanitization verification station. In this example, the node device is configured to record the state change, the issuance of the alarm, the canceling of the alarm, and other relevant information.

In another example of the node device changing from the suspect-pending state to the suspect state, while in the suspect-pending state, in response to the node device detecting a second MP identification device, i.e., an MP identification device that is different from the device that caused the suspect-pending state (i.e., valid MW/MP encounter), the node device changes its status from suspect pending to suspect and issues an alarm, which may include the display of any one or more haptic, visual, and audible indicators. The MW can take an action, such as the pressing of a button, to cancel the alarm or can re-sanitize at a sanitization verification station to effectively cancel the alarm and change the node device's state from suspect to authorized, for example, as described above.

An illustration of a situation in which a state change of suspect-pending to suspect may occur is a case where a nurse (the MW) tending to "Patient 1" of two patients (Patient 1 and Patient 2) in a double-occupancy hospital patient room. In this illustration, the MW has properly followed the pre-MW/MP encounter sanitization protocol, and the relevant sanitization verification station has issued authorization to the MW's node device. Consequently, the MW's node device has opened a monitoring session by starting the initial-contact timer. The MW then proceeds to Patient 1 in a timely manner, and the MW's node device establishes firm contact with Patient 1's (the MP) identification device. In response, the MW's node device changes its state from authorized to suspect pending, for the reasons described above. In a multi-read-range-power implementation, the MW's node device will typically be in the lowest-power mode so as to minimize the size of the read-range bubble.

In this illustration, while tending to Patient 1 and in a valid MW/MP encounter with Patient 1, the second patient, i.e., "Patient 2," experiences a health emergency that requires the MW to immediately tend to Patient 2. Consequently, the MW moves over to Patient 2 directly from tending to Patient 1, i.e., without returning to the sanitization verification station to re-sanitize and have her/his node device re-authorized. In making the switch from Patient 1 to Patient 2, the MW's node device loses contact with Patient 1's identification device and establishes firm contact with Patient 2's identification device. However, this is a violation of the sanitization protocol being implemented, because during a move from one patient to another without re-sanitizing it is assumed that the move includes a transfer of infectious material from the first patient to the second patient. Recognizing that firm contact with a Patient 2's identification device occurred in a valid MW/MP encounter for another patient, i.e., Patient 1, the node device changes its state from suspect pending to suspect and issues a suitable alarm. At this point, the MW can cancel the alarm. However, the node device records information for all of these events, information that is later uploaded to the central data processing system. It is noted that in this situation in which the health emergency of Patient 2 was so critical, the lack of re-sanitizing may be acceptable, especially because the risk of Patient 2 dying outweighed the risk that an infection was being transferred.

Data Collection and Reporting

In this example, the sanitization compliance data processing system is designed and configured to collect, save, archive, maintain, and manipulate a variety of information collected or conveyed by various components of the overall deployment, such as the registration system, sanitization verification stations, node devices, and charging stations. The data processing system is also designed and configured to generate various reports that utilize the recorded information. Following are some examples of such collected/recorded information and examples of reports that the data processing system can generate. It should be appreciated that these examples are provided for illustrative purposes and should by no means be interpreted as being exhaustive.

Examples of data received from the registration system by the sanitization compliance data processing system include an absolute RFID serial number on each patient's RFID enabled bracelet, any encrypted information on that patient's bracelet, time/date of the assignment of an RFID-enabled bracelet to a patient, an absolute RFID serial number on each RFID-enabled MW badge, any encrypted information on that HW's badge, time/date of the assignment of an RFID-enabled badge to an MW. Examples of data received from the charging stations by the sanitization compliance data processing system include identifier(s) of the node device(s) engaged with any of the charging stations, start and end times and dates of connections of node devices to charging stations, recorded data residing on the node devices when connected to a charging station after use, and other information (e.g., fault indications) concerning the charging stations and/or node devices. Examples of data received from sanitization verification stations by the sanitization compliance data processing system include event information regarding MW sanitization events and associated verification results, node device identifiers, data recorded by node devices and uploaded via the verification stations, and other information (e.g., fault indications) concerning the verification stations and/or node devices.

In particular examples, and using the method 800 of FIG. 8 as a basis for these examples: at step 805 the sanitization verification station may record information from the RFID tag of the MW at the verification station into its memory; at step 807 the verification station may add its location information to the recorded data; at step 815, the verification station may add an indication to the recorded data that the verification station has verified the MW's node device; at step 817 the verification station may add an indication to the recorded data that the MW presented their hands to the verification station; at step 819 the verification station may add an indication to the data string that the alcohol test has been completed; at step 821 the verification station may add a test identifier to the recorded data to uniquely identify the test; at step 831 the verification station may add the information uploaded from the MW's node device to the recorded data, along with an indication of whether or not the upload was completed; and at step 835 the verification station may add test results to the recorded data. As those skilled in the art will readily appreciate, the data recorded by the verification station can be uploaded to the sanitization compliance data processing system at any suitable time and in any suitable segmentation. For example, all of the data can be uploaded at once after the test results have been determined. As another example, the data can be uploaded continually as the verification station generates the data. In yet a further example, the data can be uploaded in segments, with one or a few pieces of the data being uploaded at a time. As those skilled in the art will understand, the uploading can be accomplished using any suitable communication protocol and according to any suitable scheme, such as a push or pull scheme. As with other examples, all of the forgoing examples are intended to be illustrative and not exhaustive.

In the foregoing, examples of sanitization verification event data include time/date-stamped records of the identification (via RFID tag) of each MW requesting a verification action, results of each MW's verification of alcohol level(s), and administrative events, such as equipment failure, fault, loss of connection, etc. Similarly, examples of event data collected by each node device include a time/date-stamped records indicating association with the MW carrying that node device, changes in the internal states of authorization/status, contact with patients' RFID bracelets and contents of such bracelets, alarm events, warning events, MW actions (e.g., ignore, acknowledge, etc.) in response to node events, and administrative events (e.g., battery low, fault, loss of association, etc.).

In particular examples, and using the method 900 of FIG. 9 as a basis for these examples: at step 901 the node device may record into its onboard memory information regarding the authorization from the sanitization verification station, such as the change of its state to "authorized", along with a date/time stamp; at steps 917/919, the node device may record that contact with an MP/MP identification device has been established, along with information from the MP identification device and date/time data; at steps 923 and 829, the node device may record the loss of contact with the MP, along with a date/time stamp, as well as the regaining of contact and the date/time data; at step 933, the node device may record the contact-reestablished event, also along with a date/time stamp. In addition, the node device may also be set up to record the timing out of the temporary leave timer, as well as all state changes, here changes between various pairs of "neutral," "authorized," "suspect," and "suspect pending," along with the appropriate date/time stamps.

Examples of reports and alarms that the sanitization verification data processing system of the present embodiment is designed and configured to generate include summaries of MWs' activities (e.g., sanitization events, success rates, warnings, etc.), summaries of area events in the health care facility (e.g., a summary of MWs using a particular sanitization verification station and the associated sanitization verification testing results), summaries of patient contacts with MWs and corresponding authorization or other sanitization statuses, and administrative summaries (e.g., faults, node device usage, verification station usage, etc.).

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for identifying a patient, the system comprising:
   an identification device for identifying the patient, said identification device including:
      a plurality of linked tags containing identification information identifying the patient, each tag:
         designed and configured to be readable by a standoff reading device; and
         containing linking information that allows the standoff reading device to associate the plurality of linking tags with one another; and
      a support structure designed and configured to locate the identification device proximate the patient, wherein said plurality of linking tags are supported by said support structure,
   wherein said plurality of linked tags comprise a corresponding plurality of linked radio frequency identification (RFID) tags, the system further comprising a standoff reader, possessed by a healthcare worker, designed and configured to read said plurality of linked RFID tags, said standoff reader including:
      an antenna/transponder system designed and configured to energize each of the plurality of linked RFID tags;
      a power source operatively connected to said antenna/transponder system and designed and configured to energize said antenna/transponder system with differing tag-energizing powers at differing times;
      a tag reader designed and configured for reading the identification information and linking information from each of the plurality of linked tags when in reading range;
      a power controller operatively connected to said power source and said tag reader, said power controller designed and configured to change said power source from one of said differing tag-energizing powers to another of said differing tag-energizing powers as a function of how many of the plurality of the linked tags said tag reader has identified; and
      a display indicator designed and configured to display an indication that a valid encounter between the patient and the healthcare worker is in process in response to identification of a plurality of the linked tags by the tag reader.

2. A system according to claim 1, wherein said power controller of said standoff reader is designed and configured to change from a higher one of said differing tag-energizing powers to a lower one of said tag-energizing powers as a function of said tag reader concurrently identifying at least one additional one of the plurality of linked tags.

3. A system according to claim 1, wherein the patient has an appendage, and said support structure comprises a band designed and configured to be secured around the appendage.

4. A system according to claim 3, wherein said support structure further includes a plurality of standoff supports supporting corresponding respective ones of said plurality of linked tags in spaced relation to said band when the identification device is properly engaged with the appendage of the patient.

5. A system according to claim 4, wherein the patient is a human and the appendage is an arm or a leg, said identification information comprising information assigned by a health care facility.

6. A system according to claim 1, wherein said linking information comprises a digitally encoded linking code.

7. A system according to claim 1, wherein said linking information comprises a linking sequence.

* * * * *